US008648183B2

(12) United States Patent
Suzuki et al.

(10) Patent No.: US 8,648,183 B2
(45) Date of Patent: Feb. 11, 2014

(54) MODIFIED PROMOTER

(75) Inventors: Kanako Suzuki, Tokyo (JP); Norihiro Tsukagoshi, Nagoya (JP)

(73) Assignee: Amano Enzyme Inc., Nagoya-shi (JP)

( * ) Notice: Subject to any disclaimer, the term of this patent is extended or adjusted under 35 U.S.C. 154(b) by 1749 days.

(21) Appl. No.: 10/505,171

(22) PCT Filed: Feb. 28, 2003

(86) PCT No.: PCT/JP03/02401
§ 371 (c)(1),
(2), (4) Date: Aug. 31, 2004

(87) PCT Pub. No.: WO03/080830
PCT Pub. Date: Oct. 2, 2003

(65) Prior Publication Data
US 2005/0170453 A1 Aug. 4, 2005

(30) Foreign Application Priority Data

Mar. 1, 2002 (JP) .................. 2002-055853
Dec. 6, 2002 (JP) .................. 2002-354670

(51) Int. Cl.
*C07H 21/04* (2006.01)
*G01N 33/53* (2006.01)
*C12P 21/06* (2006.01)
*C12N 1/00* (2006.01)

(52) U.S. Cl.
USPC ...... 536/24.1; 435/7.31; 435/254.1; 435/69.1; 435/254.11; 435/254.3

(58) Field of Classification Search
None
See application file for complete search history.

(56) References Cited

U.S. PATENT DOCUMENTS 5,536,661 A * 7/1996 Boel et al. .................. 435/254.3

FOREIGN PATENT DOCUMENTS

| EP | 0 238 023 | 9/1987 |
|---|---|---|
| JP | 62-272988 | 11/1987 |
| JP | 9-9968 | 1/1997 |
| JP | 2000-308491 A | 11/2000 |
| WO | 98/00528 | 1/1998 |

OTHER PUBLICATIONS

Tani, Shuji, et al., "In Vivo and in Vitro analysis of the AmyR Binding Site of the *Aspergillus nidulans agdA* Promoter; Requirement of the CGG Direct Repeat for Induction and High Affinity Binding of AmyR;"*Biosci. Biotechnol. Biochem.*, vol. 65 (7), pp. 1568-1574 (2001).
Kato, Masashi, et al. "No Factors Except for the Hap Complex increase the Taka-amylase A Gene Expression by Binding to the CCAAT Sequence in the Promoter Region;"*Biosci. Biotechnol. Biochem.*, vol. 65 (10), pp. 2340-2342 (2001).
Supplementary European Search Report for corresponding European Patent Application No. EP03 74 4981, dated Aug. 8, 2005.

Cullen et al., "Controlled Expression and Secretion of Bovine Chymosin in *Aspergillus nidulans*", Biotechnology, 5, 369-376 (1987).
Christensen et al., "High Level Expression of Recombinant Genes in *Aspergillus oryzae*", Biotechnology, 6, 1419-1422 (1988).
Kulmburg et al., "Specific Binding Sites in the alcR and alcA Promoters of the Ethanol Regulon for the CREA Repressor Mediating Carbon Catabolite Repression in *Aspergillus nidulans*", Molecular Microbiology (1993) 7(6), 847-857.
Nagata et al., "*Aspergillus nidulans* Nuclear Proteins Bind to a CCAAT Element and the Adjacent Upstream Sequence in the Promoter Region of the Starch-Inducible Taka-Amylase A Gene", Mol Gen Genet (1993) 237:251-260, cited in the International Search Report.
Petersen et al., "A New Transcriptional Activator for Amylase Genes in *Aspergillus*", Mol Gen Genet (1999) 262: 668-676 and p. 458.
Minetoki et al., "Improvement ofPromoter Activity by the Introduction of Multiple the Conserved Region III Sequence, Involved in the Efficient Expression of *Aspergillus oryzae* Amylase-Encoding Genes", Appl Microbiol Biotechnol (1998) 50: 459-467.
El-Adawi et al., "Overexpression of Protein Disulfide Isomerase in *Aspergillus*", Current Microbiology vol. 41 (2000). pp. 295-299, cited in the International Search Report.
Tani et al., A Novel Nuclear Factor, SREB, Binds to a *cis*-acting Element, SRE, Required for Inducible Expression of the *Aspergillus oryzae* Taka-Amylase A Gene in *A. nidulans*, Mol Gen Genet (2000) 263: 232-238 and p. 411, cited in the International Search Report.
Kato et al., "An *Aspergillus nidulans* Nuclear Protein, AnCP, Involved in enhancement of Taka-Amylase A Gene Expression, Binds to the CCAAT-Containing *taaG2, amdS*, and *gatA* Promoters", Mol Gen Genet (1997) 254: 119-126, cited in the International Search Report.
Tanaka et al., "An *Aspergillus oryzae* CCAAT-Binding Protein, AoCP, is Involved in the High-Level Expression of the Taka-Amylase A Gene", Curr Genet (2000) 37: 380-387, cited in the International Search Report.
Kobayashi et al., "Kojikin Taka-amylase A Idenshi no Hatsugen Seigyo Kiko", Japan Society for Bioscience, Biotechnology, and Agrochemistry, 1998 Nendo (Heisei 10 Nendo) Taikai Koen Yoshishu, Mar. 5, 1998, p. 441, S-1-3, cited in the International Search Report.
Kato et al., "Shijokin Koiki Tensha Seigyo Inshi•CCAA Ketsugo Tanpaku-shitsu ni yoru Tensha Sokushin Kiko", Japan Society for Bioscience, Biotechnology, and Agrochemistry, 1998 Nendo (Heisei 10 Nendo) Taikai Koen Yoshishu, Mar. 5, 1998, p. 461, S-4-4, cited in the International Search Report.
Suzuki et al., "Taka-amylase A Promoter o Riyo Shita Kokoritsu Jinko Promotor no Kaihatsu", Japan Society for Bioscience, Biotechnology, and Agrochemistry, 2002 Nendo (Heisei 14 Nendo) Taikai Koen Yoshishu, Mar. 5, 2002, p. 204, 3-6Ba09, cited in the International Search Report.

\* cited by examiner

*Primary Examiner* — Catherine Hibbert
(74) *Attorney, Agent, or Firm* — Edwards Wildman Palmer LLP

(57) ABSTRACT

It is intended to provide base sequences participating in the regulation of the expression of a promoter. It is also intended to modify a promoter based on the base sequence data to give a modified promoter having a high expression activity. Namely, a modified promoter constructed by inserting a first DNA fragment containing CCAATNNNNN (SEQ ID NO:1) (a first base sequence) and a second DNA fragment containing CGGNNNNNNNNGG (SEQ ID NO:2) (a second base sequence) into a promoter functioning in a filamentous fungus, wherein N in the base sequence denotes A (adenine), G (guanine), C(cytosine), or T (thymine).

10 Claims, 12 Drawing Sheets

Fig.1

SEQ ID NO: 12

```
  1 GAATTCATGG TGTTTTGATC ATTTTAAATT TTTATATGGC GGGTGGTGGG CAACTCGCTT  60
 60 CCGGGCAACT CGCTTACCGA TTACGTTAGG GCTGATATTT ACGTAAAAAT CGTCAAGGGA 120
121 TGCAAGACCA AAGTAGTAAA ACCCCGGAGT CAACAGCATC CAAGCCCAAG TCCTTCACGG 180
181 AGAAACCCCA GCGTCCACAT CACGAGCGAA GGACCACCTC TAGGCATCGG ACGCACCATC 240
241 CAATTAGAAG CAGCAAAGCG AAACAGCCCA AGAAAAAGGT CGGCCCGTCG GCCTTTTCTG 300
301 CAACGCTGAT CACGGGCAGC GATCCAACCA ACACCCTCCA GAGTGACTAG GGGCGGAAAT 360
361 TTAAAGGGAT TAATTTCCAC TCAACCACAA ATCACAGTCG TCCCCGGTAT TGTCCTGCAG 420
421 AATGCAATTT AAACTCTTCT GCGAATCGCT TGGATTCCCC GCCCCTGGCC GTAGAGCTTA 480
481 AAGTATGTCC CTTGTCGATG CGATGTATCA CAACATATAA ATACTAGCAA GGGATGCCAT 540
541 GCTTGGAGGA TAGCAACCGA CAACATCACA TCAAGCTCTC CCTTCTCTGA ACAATAAACC 600
601 CCACAGAAGG CATTT                                                  615
```

|  | Amylase Activity (U/g dry mycelia) | (ratio) |
|---|---|---|
| taaP | 1041 | 1 |
| PCCAATb | 786 | 0.8 |
| PSREb | 1319 | 1.3 |
| PCSP | 4269 | 4.1 |

▩ : CCAAT sequence (binding factor of a wide domain transcription activation factor (HAP complex))

▨ : SRE(binding factor of a transcription activation factor of a starch degrading enzyme gene cluster (AmyR))

▮ : TATA-box

⌞⌝ : inserted fragment

| Promoter | Amylase Activity | | | |
|---|---|---|---|---|
| | Starch | | Glucose | |
| | (U/g dry mycelia) | (ratio) | (U/g dry mycelia) | (ratio) |
| taaP | 916 | 1 | 25 | 1 |
| PCSb | 4601 | 5.0 | 601 | 24.1 |
| PCSPb | 6455 | 7.0 | 740 | 29.6 |
| PCSPPb | 7084 | 7.7 | 941 | 37.7 |

Fig. 6

| | Amylase Activity (U/g dry mycelia) | (ratio) |
|---|---|---|
| taaP | 1041 | 1 |
| PCmSa | 2178 | 2.1 |
| PCmSN | 1047 | 1.0 |
| PCmSb | 3237 | 3.2 |
| PCmSS | 2130 | 2.0 |

▨ : CCAAT sequence (binding factor of a wide domain transcription activation factor (HAP complex))
▨ : SRE( binding factor of a transcription activation factor of a starch degrading enzyme gene cluster (AmyR))
☐ : modified SRE
▮ : TATA-box
⌞⌝ : inserted fragment

Fig. 7

| Strain | Copy Number | Amount of Amylase (g/L) | (ratio) |
|---|---|---|---|
| ABPU1 | 0 | 0.01 | |
| taa2 | 1 | 0.29 | 1 |
| CSb17 | 1 | 1.46 | 5.0 |
| CSb16 | multiple | 9.90 | 34.1 |
| CSP6 | multiple | 6.41 | 22.1 |
| CSPb19 | multiple | 7.35 | 25.3 |

ABPU1 ; host   taa2 ; wild type promoter

Fig. 8

| Strain | Amount of Amylase (g/L) | | |
|---|---|---|---|
| | SPY medium | MPY medium | GPY medium |
| CSP6 | 6.41 | 4.86 | 2.94 |
| CSPb19 | 7.35 | 5.25 | 6.25 |

The production amount of amylase is shown as a conversion value as compared with the specific activity of Taka-amylase is 100 U/mg.

Fig. 9

| | Amylase Activity (U/g dry mycelia) | (ratio) |
|---|---|---|
| taaP | 1041 | 1 |
| PCmSb | 3237 | 3.2 |
| PsCmSb | 1634 | 1.6 |

■ : CCAAT sequence (binding factor of a wide domain transcription activation factor (HAP complex))
▨ : SRE(binding factor of a transcription activation factor of a starch degrading enzyme gene cluster (AmyR))
□ : modified SRE
▮ : TATA-box
⋯ : inserted fragment

Fig. 11

| Promoter | Amylase Activity | | | |
|---|---|---|---|---|
| | A. oryzae KBN616 | | A. oryzae KBN6217 | |
| | (U/g mycelia) | (ratio) | (U/g mycelia) | (ratio) |
| non-recombinant strain | 377 | 1 | 13003 | 1 |
| PCSPb | 21702 | 57.6 | 137179 | 10.6 |

Fig. 1 2

| Promoter | Laccase Activity | |
|---|---|---|
| | (Δ O.D. / 0.1ml) | (ratio) |
| non-recombinant strain | 0 | - |
| taaP | 174 | 1 |
| PCSPb | 136 | 0.8 |
| PCSPPb | 281 | 1.6 |

US 8,648,183 B2

SEQUENCE LISTING

```
<160> NUMBER OF SEQ ID NOS: 40

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: an enhancer
      sequence
<220> FEATURE:
<221> NAME/KEY: misc_feature
<222> LOCATION: (6)..(11)
<223> OTHER INFORMATION: n stands for any base.

<400> SEQUENCE: 1
ccaatnnnnn n                                                          11

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: an enhancer
      sequence
<220> FEATURE:
<221> NAME/KEY: misc_feature
<222> LOCATION: (4)..(12)
<223> OTHER INFORMATION: n stands for any base.

<400> SEQUENCE: 2
cggnnnnnnn nngg                                                       14

<210> SEQ ID NO 3
<211> LENGTH: 11
<212> TYPE: DNA
```

```
<213> ORGANISM: Artificial Sequence
<220> FEATURE:
<223> OTHER INFORMATION: Description of Artificial Sequence: an enhancer
      sequence

<400> SEQUENCE: 3
ccaattagaa g                                                              11

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: an enhancer
      sequence
<220> FEATURE:
<221> NAME/KEY: misc_feature
<222> LOCATION: (5)..(5)
<223> OTHER INFORMATION: n stands for any base.
<220> FEATURE:
<221> NAME/KEY: misc_feature
<222> LOCATION: (10)..(10)
<223> OTHER INFORMATION: n stands for any base.

<400> SEQUENCE: 4
cgghnwwwwn whgg                                                           14

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: an enhancer
      sequence

<400> SEQUENCE: 5
cggwwwwwww whgg                                                           14

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: an enhancer
      sequence

<400> SEQUENCE: 6
cggaaattta aagg                                                           14

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: an enhancer
      sequence

<400> SEQUENCE: 7
cggaatttaa acgg                                                           14

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: an enhancer
      sequence

<400> SEQUENCE: 8
```

```
cggaaattta acgg                                                 14

<210> SEQ ID NO 9
<211> LENGTH: 128
<212> TYPE: DNA
<213> ORGANISM: Artificial Sequence
<220> FEATURE:
<223> OTHER INFORMATION: Description of Artificial Sequence:a DNA
      fragment including CCAAT sequence and SRE

<400> SEQUENCE: 9
ccaattagaa gcagcaaagc gaaacagccc aagaaaaagg tcggcccgtc ggccttttct    60
gcaacgctga tcacgggcag cgatccaacc aacaccctcc agagtgacta ggggcggaaa   120
tttaaagg                                                           128

<210> SEQ ID NO 10
<211> LENGTH: 196
<212> TYPE: DNA
<213> ORGANISM: Artificial Sequence
<220> FEATURE:
<223> OTHER INFORMATION: Description of Artificial Sequence:a DNA
      fragment including CCAAT sequence and SRE

<400> SEQUENCE: 10
ctgcagacca cctctaggca tcggacgcac catccaatta gaagcagcaa agcgaaacag    60
cccaagaaaa aggtcggccc gtcggccttt tctgcaacgc tgatcacggg cagcgatcca   120
accaacaccc tccagagtga ctaggggcgg aaatttaaag ggattaattt ccactcaacc   180
acaaatcaca ctgcag                                                  196

<210> SEQ ID NO 11
<211> LENGTH: 193
<212> TYPE: DNA
<213> ORGANISM: Artificial Sequence
<220> FEATURE:
<223> OTHER INFORMATION: Description of Artificial Sequence:a DNA
      fragment including CCAAT sequence and SRE

<400> SEQUENCE: 11
ctcgagaggc atcggacgca ccatccaatt agaagcagca aagcgaaaca gcccaagaaa    60
aaggtcggcc cgtcggcctt ttctgcaacg ctgatcacgg gcagcgatcc aaccaacacc   120
ctccagagtg actaggggcg gaaatttaaa gggattaatt tccactcaac acaaatcac   180 agtcggcggc cgc                                                     193

<210> SEQ ID NO 12
<211> LENGTH: 615
<212> TYPE: DNA
<213> ORGANISM: Aspergillus oryzae
<220> FEATURE:
<221> NAME/KEY: promoter
<222> LOCATION: (1)..(615)
<223> OTHER INFORMATION:

<400> SEQUENCE: 12
gaattcatgg tgttttgatc attttaaatt tttatatggc gggtggtggg caactcgctt    60
ccgggcaact cgcttaccga ttacgttagg gctgatattt acgtaaaaat cgtcaaggga   120
tgcaagacca aagtagtaaa accccggagt caacagcatc caagcccaag tccttcacgg   180
agaaacccca gcgtccacat cacgagcgaa ggaccacctc taggcatcgg acgcaccatc   240
caattagaag cagcaaagcg aaacagccca agaaaaggt cggcccgtcg gccttttctg   300
caacgctgat cacgggcagc gatccaacca acaccctcca gagtgactag gggcggaaat   360
```

```
ttaaagggat taatttccac tcaaccacaa atcacagtcg tccccggtat tgtcctgcag    420
aatgcaattt aaactcttct gcgaatcgct tggattcccc gccctggcc gtagagctta    480 aagtatgtcc cttgtcgatg cgatgtatca acacatataa atactagcaa gggatgccat    540
gcttggagga tagcaaccga caacatcaca tcaagctctc ccttctctga acaataaacc    600
ccacagaagg cattt                                                    615
```

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: a PCR
      primer designed for amplifying CCAAT sequence

<400> SEQUENCE: 13

```
ccgctcgagg caccatccaa ttagaagcgc ggccgctaaa ctat                     44
```

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: a PCR
      primer designed for amplifying CCAAT sequence

<400> SEQUENCE: 14

```
atagtttagc ggccgcgctt ctaattggat ggtgcctcga gcgg                     44
```

<210> SEQ ID NO 15
<211> LENGTH: 46
<212> TYPE: DNA
<213> ORGANISM: Artificial Sequence
<220> FEATURE:
<223> OTHER INFORMATION: Description of Artificial Sequence: a PCR
      primer designed for amplifying SRE

<400> SEQUENCE: 15

```
gactagttaa cctaggggcg gaaatttaac gggatgttaa ctagtc                   46
```

<210> SEQ ID NO 16
<211> LENGTH: 46
<212> TYPE: DNA
<213> ORGANISM: Artificial Sequence
<220> FEATURE:
<223> OTHER INFORMATION: Description of Artificial Sequence: a PCR
      primer designed for amplifying SRE

<400> SEQUENCE: 16

```
gactagttaa catcccgtta aatttccgcc cctaggttaa ctagtc                   46
```

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: a PCR
      primer designed for amplifying a DNA fragment including CCAAT
      sequence and SRE

<400> SEQUENCE: 17

```
aaactgcaga ccacctctag gcatcggacg                                     30
```

<210> SEQ ID NO 18
<211> LENGTH: 30

-continued

```
<212> TYPE: DNA
<213> ORGANISM: Artificial Sequence
<220> FEATURE:
<223> OTHER INFORMATION: Description of Artificial Sequence: a PCR
      primer designed for amplifying a DNA fragment including CCAAT
      sequence and SRE

<400> SEQUENCE: 18
tttctgcagt gttgatttgt ggttgagtgg                                          30

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: a PCR
      primer designed for amplifying a DNA fragment including CCAAT
      sequence and SRE

<400> SEQUENCE: 19
cggctcgagg catcggacgc accatcc                                             27

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: a PCR
      primer designed for amplifying a DNA fragment including CCAAT
      sequence and SRE

<400> SEQUENCE: 20
atagtttagc ggccgccgac tgtgatttgt ggttgagtgg                               40

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence:a primer for
      site-directed mutagenesis

<400> SEQUENCE: 21
cgcttggatt ccccgcccgc ggccgcagag cttaaagtat gtccc                         45

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence:a primer for
      site-directed mutagenesis

<400> SEQUENCE: 22
gaatgcaatt taaactcttc ctcgagtcgc ttggattccc cgccc                         45

<210> SEQ ID NO 23
<211> LENGTH: 47
<212> TYPE: DNA
<213> ORGANISM: Artificial Sequence
<220> FEATURE:
<223> OTHER INFORMATION: Description of Artificial Sequence:a primer for
      site-directed mutagenesis

<400> SEQUENCE: 23
gtagtaaaac cccggagtca gcggccgcca agcccaagtc cttcacg                       47

<210> SEQ ID NO 24
```

-continued

```
<211> LENGTH: 41
<212> TYPE: DNA
<213> ORGANISM: Artificial Sequence
<220> FEATURE:
<223> OTHER INFORMATION: Description of Artificial Sequence:a primer for
      site-directed mutagenesis

<400> SEQUENCE: 24
cgtcaaggga tgcaagactc gagtagtaaa accccggagt c                    41

<210> SEQ ID NO 25
<211> LENGTH: 47
<212> TYPE: DNA
<213> ORGANISM: Artificial Sequence
<220> FEATURE:
<223> OTHER INFORMATION: Description of Artificial Sequence:a primer for
      site-directed mutagenesis

<400> SEQUENCE: 25
gcaccatcca attagaagcg cggccgcgaa acagcccaag aaaaagg              47

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence:a primer for
      site-directed mutagenesis

<400> SEQUENCE: 26
taaagtatgt cactagtcga tgcgat                                     26

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence:a primer for
      site-directed mutagenesis

<400> SEQUENCE: 27
taggggcgga atttaaacgg gattaa                                     26

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence:a PCR primer
      designed for amplifying a DNA fragment including CCAATsequence

<400> SEQUENCE: 28
gaagatctct gtttcgcttt gctgcttc                                   28

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence:a PCR primer
      designed for amplifying a DNA fragment including SRE

<400> SEQUENCE: 29
gaagatcttc cagagtgact aggggcgg                                   28

<210> SEQ ID NO 30
<211> LENGTH: 14
<212> TYPE: DNA
```

```
<213> ORGANISM: Artificial Sequence
<220> FEATURE:
<223> OTHER INFORMATION: Description of Artificial Sequence:a partialy
      modified SRE

<400> SEQUENCE: 30
cggaaattta atta                                                        14

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence:a PCR primer
      designed for mutating SRE

<400> SEQUENCE: 31
ggggcggaaa tttaacggga ttaatttcc                                        29

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence:a PCR primer
      designed for mutating SRE

<400> SEQUENCE: 32
cggaaattta attagattaa tttcc                                            25

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence:a PCR primer

<400> SEQUENCE: 33
tatgtcgacc caagccgctg ctggaattga                                       30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence:a PCR primer

<400> SEQUENCE: 34
gaaaagcttg atcaataccg tacgggagat                                       30

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence:a PCR primer

<400> SEQUENCE: 35
ggaattcatg gtgttttgat c                                                21

<210> SEQ ID NO 36
<211> LENGTH: 37
<212> TYPE: DNA
<213> ORGANISM: Artificial Sequence
<220> FEATURE:
<223> OTHER INFORMATION: Description of Artificial Sequence:a PCR primer

<400> SEQUENCE: 36
```

```
gagaccacca cgcgacatgc ataaatgcct tctgtgg                                  37

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence:a PCR primer

<400> SEQUENCE: 37
ccatgcattt ctttatcatt ggag                                                24

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence:a PCR primer

<400> SEQUENCE: 38
ccgagctctg gtatagtatc ttgaatgtat c                                        31

<210> SEQ ID NO 39
<211> LENGTH: 14
<212> TYPE: DNA
<213> ORGANISM: Aspergillus niger

<400> SEQUENCE: 39
cggtcttttg tcgg                                                           14

<210> SEQ ID NO 40
<211> LENGTH: 14
<212> TYPE: DNA
<213> ORGANISM: Aspergillus oryzae

<400> SEQUENCE: 40
cggcgaattc acgg                                                           14
```

MODIFIED PROMOTER

This is a 371 of PCT/JP03/02401, filed on Feb. 28, 2003, which is hereby incorporated by reference.

TECHNICAL FIELD

The present invention relates to an improvement in a promoter used for producing a protein. More particularly, the present invention relates to a modified promoter obtained by modifying a promoter capable of functioning in a filamentous fungus. Furthermore, the present invention relates to a protein production system using the modified promoter.

BACKGROUND ART

It has been confirmed that *Aspergillus* filamentous fungi secrete a large amount of various enzyme proteins to the outside of the fungus body. For example, it is said that industrially used *Aspergillus oryzae* produces several tens grams or more of enzyme proteins per litter of culture medium. Thus, the use of filamentous fungi as a host enables secretion production of homogenous and heterogeneous proteins with high productivity. Furthermore, many strains of filamentous fungi have conventionally been used for production of brewing products, and so it can be said that the filamentous fungi are suitable for producing proteins also from the viewpoint of safety. Therefore, in recent years, examples in which filamentous fungi are used as a host for producing useful proteins by gene recombination has been reported. When producing secretory proteins, the amount of produced proteins is determined by various factors in the process from the expression of a targeted protein to the modification of the protein. The most effective means for increasing the production amount of proteins is to enhance the transcription efficiency, that is, to increase the amount of transcription. From such a viewpoint, promoters derived from various filamentous fungi have been isolated and protein production systems using the promoters have been reported to date. For example, a promoter of amylase gene of *Aspergillus oryzae* (see, for example, JP 62 (1987)-272988A and Biotechnology, 5, 368 (1987)), a promoter of glucoamylase gene of *Aspergillus niger* (see, for example, Biotechnology, 6, 1419 (1988)) have been isolated and used.

Under the present situation, although some promoters are used, little about a gene expression mechanism of the promoter is clarified. To date, only a factor involved in catabolite repression regulation as a transcriptional regulation factor (see, for example, Mol. Microbiol., 7, 847-857 (1993)), a binding factor of a HAP complex that is a wide-domain transcription activation factor (see, for example, Mol. Gen. Genet., 237, 251-260 (1993)), a transcription activation factor of starch degrading enzyme gene cluster (see, for example, Mol. Gen. Genet., 262, 668-676(1999)), and the like, have been reported. Therefore, examples of attempts that have been carried out to produce useful proteins using filamentous fungi with high efficiency include, mainly, producing bacteria with high productivity by classical breeding, and isolating naturally occurring higher expression promoter. However, such attempts have required much labor and been much dependent upon the contingency, so that possibility of obtaining high expression promoter is low. On the other hand, if the capability of expression control of promoters is improved, such problems could radically be resolved. Also to date, as an attempt to improve the capability of expression control, modification of α-glucosidase gene of *Aspergillus oryzae* has been reported (see, for example, JP 9(1999)-9968A and Appl. Microbiol. Biotechnol., 50, 459-467 (1998)). However, although with such modified promoter, the capability of expression control is improved to some extent, it cannot be said that such a sufficient expression property as to carry out the production of proteins can be obtained. There remains a demand for development of a promoter capable of transcribing the targeted protein gene with high efficiency.

The present invention was completed based on the above-mentioned background and has an object to provide a base sequence involved in expression regulation by a promoter. Furthermore, it is also an object of the present invention to provide a modified promoter with high expression activity by modifying a promoter based on the information of this base sequence. Furthermore, it is also an object of the present invention to construct an expression system (production system) of proteins using the filamentous fungus as a host by using this modified promoter.

DISCLOSURE OF INVENTION

With the view of the above-mentioned objects, the present investors have carried out the following investigations. That is to say, the present inventors have paid attention to Taka-amylase A gene of *Aspergillus oryzae* which is known to have a high promoter activity, and, by modifying this promoter, attempted to obtain a modified promoter with a higher transcription activity. As a result, the present inventors have found a pair of sequences capable of enhancing the transcription activity by inserting thereof into a promoter region. By using the promoter modified by the sequences, it was possible to obtain an *Aspergillus nidulans* strain capable of producing amylase with high productivity. From further investigation, in a strain into which multiple copies of amylase genes having the modified promoter, more efficient production of proteins was observed.

From the investigation result mentioned above, the finding was obtained in that the newly discovered sequences are extremely effective in modification of a promoter region and that the use of this makes it possible to construct a more efficient protein expression system using filamentous fungi as a host.

On the other hand, the effect in the case where a plurality of sequences are used to modify the promoter was investigated by using an amylase expression system as a model. As a result, it was determined that if a modified promoter in which a plurality of the sequences are integrated was used, even if glucose was used as a carbon source, excellent production of amylase can be achieved. That is to say, although a wild type strain is subjected to expression repression (catabolite repression) by glucose in a medium, it was shown that the use of a modified promoter in which a plurality of the sequences were inserted made it possible to remove this catabolite repression. This suggested that the newly discovered sequences should be also effective in blocking or removing a mechanism involved in the repression of promoter activity.

Furthermore, when the present inventors have paid attention to the enhancer function of SRE and attempted to improve thereof by providing various mutations, we successfully obtained a sequence having more excellent enhancer function than that of SRE.

The present invention was completed based on the above-mentioned findings and provides the following configurations.

[1] A modified promoter constructed by inserting a first DNA fragment including CCAATNNNNN (a first base sequence: SEQ ID NO: 1) and a second DNA fragment including CGGNNNNNNNNNGG (a second base sequence: SEQ ID NO: 2) into a promoter capable of functioning in a filamentous fungus.

[2] The modified promoter according to [1], wherein said first base sequence is CCAATTAGAAG (SEQ ID NO: 3).

[3] The modified promoter according to [1] or [2], wherein said second base sequence is CGGHNWWWWNWHGG (SEQ ID NO: 4).

[4] The modified promoter according to [1] or [2], wherein said second base sequence is CGGWWWWWWWWHGG (SEQ ID NO: 5).

[5] The modified promoter according to [1] or [2], wherein said second base sequence is CGGAAATTTAAAGG (SEQ ID NO: 6), CGGAATTTAAACGG (SEQ ID NO: 7) or CGGAAATTTAACGG (SEQ ID NO: 8).

[6] The modified promoter according to any of [1] to [5] wherein the first DNA fragment and the second DNA fragment are inserted so that they are arranged sequentially from the 5'-end side to the 3'-end side of said promoter.

[7] The modified promoter according to [6], wherein said first DNA fragment and said second DNA fragment are inserted at the 5'-end side that is upstream to a CCAAT sequence existing in said promoter or at the 3'-end side that is downstream to a SRE region existing in the promoter region.

[8] The modified promoter according to any of [1] to [7], wherein a plurality of said first DNA fragments and a plurality of said second DNA fragments are inserted.

[9] The modified promoter according to [8], wherein the same number of said first DNA fragments and said second DNA fragments are inserted.

[10] The modified promoter according to [9], wherein one first DNA fragment and one second DNA fragment are combined as a pair, and in each pair, said first DNA fragment and said second DNA fragment are inserted so that the first DNA fragment is located at the 5'-end side of said promoter.

[11] A modified promoter constructed by integrating one to several of either a DNA fragment having a base sequence of SEQ ID NO: 9, or a DNA fragment obtained by partial modification of the DNA fragment and which has an enhancer function, into a promoter capable of functioning in a filamentous fungus.

[12] The modified promoter according to any of [1] to [11], wherein said promoter capable of functioning in a filamentous fungus is a promoter of Taka-amylase of *Aspergillus oryzae*.

[13] A DNA fragment having an enhancer function consisting of a base sequence of CGGAATTTAAACGG (SEQ ID NO: 7) or CGGAAATTTAACGG (SEQ ID NO: 8).

[14] A modified promoter capable of functioning in a filamentous fungus, comprising a DNA fragment according to [13].

[15] A vector in which the modified promoter according to any of [1] to [12] and [14] is integrated.

[16] A vector in which the modified promoter according to any of [1] to [12] and [14] is integrated and further a structural gene of a targeted protein is integrated under control of the modified promoter.

[17] A transformed filamentous fungus comprising the vector according to [16] capable of expressing said structural gene.

[18] A filamentous fungus comprising the modified promoter according to any of [1] to [12] and [14], and a structure gene encoding a targeted protein and being under control of the modified promoter.

[19] A method for producing a protein, the method comprising: culturing the filamentous fungus according to [18] under conditions capable of producing protein; and collecting the produced protein.

BRIEF DESCRIPTION OF DRAWINGS

FIG. 1 shows a sequence of a promoter region of a Taka-amylase A gene (*Aspergillus oryzae*).

FIG. 6 is a table summarizing amylase activities measured in Example 10. Left to the table, insertion positions of a CCAAT-mSRE fragment in each modified promoter are schematically shown. A dotted box shows an inserted fragment. taaP denotes a wild type promoter. Furthermore, PCmSa, PCmSN, PCmSb and PCmSS are modified promoters into which one CCAAT-mSRE fragment is inserted in the different positions, respectively.

FIG. 7 is a table summarizing the production amount of amylase produced by culturing each transformant obtained in Example 11 in a SPY medium for five days. ABPU1 denotes a host used; and taa2 denotes a strain having a wild type promoter. The production amount of amylase is shown as a conversion value as compared with the specific activity of Taka-amylase is 100 U/mg.

FIG. 8 is a table summarizing amylase activities measured in Example 12 and shows the production amount of amylase produced by culturing a fungus having a modified promoter for five days with varying carbon sources. The production amount of amylase is shown as a conversion value as compared with the specific activity of Taka-amylase is 100 U/mg.

FIG. 9 is a table summarizing the amylase activity measured in Example13. Left to the table, insertion position of a CCAAT-mSRE fragment or sCCAAT-mSRE fragment in each modified promoter is schematically shown. A dotted box shows an inserted fragment. taaP denotes a wild type promoter; PCmSb denotes a modified promoter into which a CCAAT-mSRE fragment is inserted; and PsCmSb denotes a modified promoter into which a sCCAAT-mSRE fragment is inserted.

FIG. 11 a table summarizing amylase activities measured in Examples 15 and 16. Non-recombinant strain denotes a strain that is not transformed; and PCSPb is a strain having a promoter in which two CCAAT-SRE fragments are inserted.

FIG. 12 is a table summarizing laccase activities measured in Examples 17 and 18. Non-recombinant strain denotes a strain that is not transformed; PCSPb denotes a promoter into which two CCAAT-SRE fragments are inserted, and PCSPPb denotes a promoter having three CCAAT-SRE fragments, respectively.

BEST MODE FOR CARRYING OUT THE INVENTION

Figure 2:
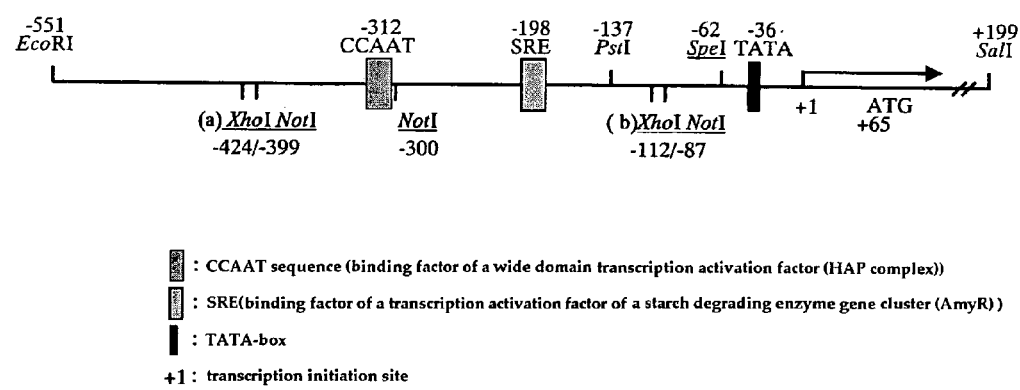
FIG. 2 is a schematic view showing a promoter region of a Taka-amylase A gene (*Aspergillus oryzae*) and showing the position of transcriptional regulation factor binding sequence (CCAAT sequence and SRE) and the position into which mutation is introduced. A restriction enzyme site introduced by a site-directed mutation is underlined. CCAAT denotes a CCAAT sequence (binding factor of a wide domain transcription activation factor (HAP complex)), SRE denotes a binding factor of a transcription activation factor of a starch degrading enzyme gene cluster (AmyR), TATA denotes a TATA-box, and +1 denotes a transcription initiation site, respectively.

Hereinafter, the present invention is described in more detail. Note here that a function capable of enhancing the promoter activity in the present invention is referred to as an "enhancer function."

Firstly, the present inventors paid attention to a CCAAT sequence (SEQ ID NO: 3) and SRE (SEQ ID NO: 6) of the promoter region being widely conserved in genus *Aspergillus*, and investigated the influence on the promoter activity when theses sequences are exogenously inserted in the promoter region. First of all, a plasmid including a promoter region of a Taka-amylase A gene of an *Aspergillus oryzae* strain JCM02239 was constructed. On the other hand, a DNA fragment including a CCAAT sequence and a DNA fragment including SRE were obtained, respectively. Then, each DNA fragment was singly inserted into a promoter region of the above-mentioned plasmid so as to construct a modified promoter. Next, a plasmid including each of the modified promoters and coding region of the Taka-amylase A gene was prepared. By using the thus obtained plasmids, respectively, *Aspergillus nidulans* was transformed. The transformants were compared with each other. As a result, the amylase activity of the transformant having a modified promoter in which the CCAAT sequence or the SRE was inserted was lower than or substantially equal to that of transformant having a promoter that was not modified. Furthermore, when a case where the promoter was modified by inserting a plurality of the CCAAT sequences or a plurality of the SREs were inserted so as to modify the promoter was investigated, similarly the increase in the promoter activity was not observed. From the above-mentioned results, it was anticipated that even if a promoter is modified by inserting the CCAAT sequence or the SRE singly into the promoter region, the promoter activity cannot increase.

Then, the change in the promoter activity when the promoter was modified with the combination of the CCAAT sequence and the SRE was investigated. Firstly, a DNA fragment including the CCAAT sequence and the SRE (CCAAT-SRE fragment: SEQ ID NO: 9) was produced using a promoter region of a Taka-amylase A gene of an *Aspergillus oryzae* strain JCM02239 as a template. By using this DNA fragment, a modified promoter of a Taka-amylase A gene was constructed by the same method as mentioned above. Then, after a plasmid including this modified promoter and a coding region of a Taka-amylase A gene was constructed, by using this plasmid, transformed strain of *Aspergillus nidulans* was obtained. When the amylase activity of this transformed strain was measured, the significant increase in the promoter activity was obtained as compared with the transformed strain (wild type strain) having a promoter that was not modified. From this, it was determined that by inserting both the CCAAT sequence and the SRE into the promoter region, a modified promoter with higher activity could be produced.

Herein, generally, even if a part of bases of a DNA sequence is substituted, the function of the DNA sequence can be occasionally maintained. Meanwhile the CCAAT sequence is known as a binding sequence of wide domain transcription activation factor (HAP). It was reported that for this binding, the CCAAT sequence at the 5'-end side was important. Therefore, even if bases other than those of the CCAAT sequence at the 5'-end side are substituted, it is expected that the enhancer function of the CCAAT sequence is maintained.

On the other hand, the present inventors investigated whether or not the enhancer function of the SRE was maintained in a case where a part of the bases is substituted. Firstly, by a PCR reaction using a primer designed so that a part of the SRE was substituted, a DNA fragment including the CCAAT sequence and the SRE (CGGAATTTAAACGG: SEQ ID NO: 7) with a part of the bases substituted of the promoter region of a Taka-amylase A gene was obtained. Then, by the same method as mentioned above, a modified promoter in which this DNA fragment was inserted and modification was carried out was produced. Then, a transformed strain of *Aspergillus nidulans* into which a Taka-amylase A gene having the modified promoter was integrated was obtained. When the amylase activity of this transformed strain was measured, the increase in the amylase activity was observed substantially the same as that obtained when a promoter modified by using a CCAAT-SRE fragment as mentioned above. Thus, it was shown that even if a part of the bases of SRE was substituted, the enhancer function could be occasionally maintained. In particular, it was shown that even if the bases in the 6th, 9th and 12th from the 5'-end side were substituted, the enhancer function of the SRE was hardly affected.

After obtaining the above-mentioned findings, in order to locate a part (sequence) of the SRE that is important in exhibiting the enhancer function, a modified promoter in which the SRE existing in a wild type promoter is provided with a mutation was constructed and the constructed promoter was examined. As a result, when the base in the 12th position from the 5'-end side of the SRE is substituted by C, the phenomenon in which the enhancer function of the SRE is not only maintained but also enhanced was observed. From this result, it was determined that even if the base in the 12th position from the 5'-end side was substituted, the enhancer function of the SRE can be maintained and that the sequence (CGGAAATTTAACGG: SEQ ID NO:8) of the SRE in which the base in the 12th position from the 5'-end side was substituted by C had more excellent enhancer function.

On the other hand, as a wild strain of Aspergillus genera, a strain in which the sequence of the SRE is CGGTCTTTTGTCGG (SEQ ID NO: 39) (α-glucosidase of Aspergillus nidulans) and a strain in which the sequence of the SRE has a CGGCGAATTCACGG (SEQ ID NO: 40) (glucoamylase of Aspergillus oryzae) are known. Furthermore, it has not been reported that in these wild strains, a decrease of promoter activity is not reported. When these sequences are compared with the SRE existing in the promoter in a Taka-amylase gene of Aspergillus oryzae, bases in the positions of 4th, 5th, 7th, 10th and 11th from the 5'-end side are not common to each other. Consequently, it is thought that these bases have a low level of contribution to the enhancer function of the SRE. That is to say, it is thought that even if these bases are substituted by others, the enhancer function of the SRE may be maintained with high probability. Specifically, even if the base in the 4th position from the 5'-end side is T or C; the base in the 5th position from the 5'-end side is C or G; the base in the 7th position from thej 5'- end side is A; the base in the 10th position from the 5'-end side is G or C; and the base in the 11th position from the 5'-end side is T, the enhancer function is expected to be maintained. However, when the binding property due to the structure of the individual structure is considered, it is thought to be desirable that the bases in the 6th to 9th and 11th positions from the 5'-end side, and further preferably the bases in the 4th to 11th positions from the 5'-end side is A or T.

From the above-mentioned findings and consideration, the base sequence of the first DNA fragment used for modification of the promoter region of the present invention is preferably CCAATTAGAAG (SEQ ID NO: 3). On the other hand, the base sequence of the second DNA fragment is preferably CGGHNWWWWNWHGG (SEQ ID NO: 4), more preferably CGGWWWWWWWWHGG (SEQ ID NO: 5), and yet further preferably CGGAAATTTAAAGG (SEQ ID NO: 6), CGGAATTTAAACGG (SEQ ID NO: 7) or CGGAAATT-TAACGG (SEQ ID NO: 8). Herein, N in the base sequence denotes A (adenine), G (guanine), C(cytosine), or T (thymine); W denotes A (adenine) or T (thymine); and H denotes A (adenine), C (cytosine) or T (thymine), respectively.

Furthermore, as mentioned above, since it was determined that the sequence obtained by substituting the base in the 12th position from the 5'-end side of the SRE by C has a more excellent enhancer function per se, it can be said that a promoter can be modified by only this sequence. That is to say, the sequence (CGGAAATTTAACGG:SEQ ID NO: 8) is useful for modifying a promoter and by using the sequence singly, it is possible to construct a promoter with high activity. Furthermore, since also the above-mentioned sequence CGGAATTTAAACGG (SEQ ID NO: 7) is recognized to have the same level of enhancer function as that of a wild type SRE, although the results in this case was obtained by using it together with the CCAAT sequence, it can be expected that this sequence is used for enhancing the promoter activity singly. Note here that "use" herein includes: constructing the above-mentioned sequence by substituting a part of the SRE that originally exists in a wild type promoter (including a promoter to which other modification was already provided); and inserting a DNA fragment containing the above-mentioned sequence into a wild type promoter (including a promoter to which other modification was already provided). Furthermore, "singly" herein means that the above-mentioned first DNA fragment is not used at the same time.

On the other hand, the present inventors have investigated the relation between the modification of the promoter region by inserting the CCAAT-SRE fragment and the catabolite repression. Firstly, a promoter in which one copy of CCAAT-SRE fragment was inserted and promoters in which two copies and three copies of CCAAT-SRE fragments were respectively inserted were prepared. Then, the transformant into which a Taka-amylase gene including any of a promoter to which the modification is not provided and a modified promoter is inserted were respectively obtained, and the amylase activities of fungi grown in a medium containing glucose as a carbon source were compared with each other. As a result, in a fungus having a promoter to which the modification is not provided, the amylase activity was deteriorated because the catabolite repression was applied; but in the fungus to which a CCAAT-SRE fragment was inserted, the catabolite repression is low and about 37 times or more of amylase activity than that of the fungus having a promoter to which the modification is not provided was observed. According to such findings, from the viewpoint of capable of removing the catabolite repression, it is preferable that a promoter is modified by inserting a plurality of CCAAT fragments and SRE fragments into a promoter.

The first DNA fragment and the second DNA fragment can be synthesized by using, for example, a commercially available DNA synthesizer. Furthermore, for example, they can be prepared by a PCR method with appropriate primers by using a promoter region of a Taka-amylase A gene of *Aspergillus oryzae* as a template.

Also, the modified promoter of the present invention can be prepared by preparing one DNA fragment including the first DNA fragment and the second DNA fragment, and then integrating this into a promoter capable of functioning in filamentous fungi. For example, such a DNA fragment can be prepared as follows, that is, a promoter including sequences corresponding to the first DNA fragment and the second DNA fragment is selected from promoters in *Aspergillus* genera, and a PCR method using this promoter as a template is carried out. An example of the preferable promoter to be used as a template can include a promoter of a Taka-amylase A gene of *Aspergillus oryzae* (SEQ ID NO: 12). One example of the base sequence of the DNA fragment used for modification of a promoter in the present invention is shown in SEQ ID NO: 9. This DNA fragment (CCAAT-SRE fragment) is a part (positions from 240to 367 (positions −312 to −185 when transcription initiation site is +1)) of the promoter region of a Taka-amylase A gene of *Aspergillus oryzae*. Note here that a DNA fragment obtained by modifying a part of this fragment can be used for modification of a promoter region as long as it has a function (enhancer function) capable of enhancing the promoter into which it is integrated. Herein, a part of modification denotes that a part of the bases constitute the DNA fragment is substituted, deleted, or one to several bases are added or inserted. Allowable degree of such modification is dependent upon a site on the DNA fragment to be modified. As mentioned above, since a portion that is important for enhancer function is a sequence portion corresponding to the first DNA fragment and the second DNA fragment, it is preferable that this sequence portion is less modified. On the other hand, since it is anticipated that other portions are not directly responsible for the enhancer function, it is thought that relatively large modification can be allowed. For example, about 1 to 20, preferably 1 to 10, and furthermore preferably 1 to 5 bases can be substituted, deleted, and added. Note here that such modification includes insertion of a restriction enzyme recognition sequence to the 5'-end, 3'-end or other sites, or addition of a sequence coding signal peptide, and the like.

According to the present invention, the first DNA fragment and the second DNA fragment (hereinafter, these DNA fragments and a DNA fragment including them will also be referred to as "DNA fragment having a enhancer function") are inserted in a promoter capable of functioning in filamentous fungi and thus a modified promoter is constructed, but the insertion site of these DNA fragments is not particularly limited. However, a promoter having a CCAAT sequence and SRE is employed as a promoter to be modified, these DNA fragments are preferably inserted in sites other than the site between these two sequences. That is to say, it is preferable that these DNA fragments having an enhancer function are inserted in the site at the 5'-end side with respect to the CCAAT sequence or in the site at the 3'-end side with respect to the SRE.

By inserting a plurality of the first DNA fragments and a plurality of the second DNA fragments into a promoter capable of functioning in filamentous fungi, the modified promoter of the present invention can prepared. In this case, it is preferable that the number of the first DNA fragments and the number of the second DNA fragments are the same as each other. Furthermore, it is preferable that one first DNA fragment and one second DNA fragment are combined as a pair, and in each pair, the first DNA fragment and the second DNA fragment are inserted so that the first DNA fragment is located at the 5'-end side of the promoter.

In the case where a DNA fragment including the first DNA fragment and the second DNA fragment is used, by inserting a plurality of such DNA fragments, a promoter may be modified. Also in this case, a promoter having a CCAAT sequence and SRE is employed as a promoter to be modified, the DNA fragments are preferably inserted in sites other than the site between these two sequences.

By modifying a promoter by integrating a plurality of DNA fragments having an enhancer function, further improvement of the promoter activity can be expected. At this time, the number of DNA fragments to be integrated is more preferably two than one, and more preferably three than two. Furthermore, as shown in the below mentioned Examples, the insertion of the DNA fragment can block or release the mechanism working for suppressing the promoter activity (it is shown to be effective in removing the catabolite repression in producing amylase).

The kind of the promoter capable of functioning in filamentous fungi of the present invention is not particularly limited as long as it has a nature of functioning in filamentous fungi. Examples thereof include a promoter of gene encoding proteins in microorganism such as genus *Aspergillus*, genus *Penicillium*, genus *Trichoderma*, etc. Specifically, a promoter of gene encoding a-amylase, glucoamylase, a-glucosidase, etc. of genus *Aspergillus* can be used. Among them, a promoter of a Taka-amylase of *Aspergillus oryzae* is preferably used. These promoters can be obtained from a microorganism possessing them by genetic engineering technique such as a restriction enzyme treatment, a PCR method, etc. Furthermore, when a vector in which a targeted promoter is integrated is available, the promoters can be obtained from the vector by genetic engineering technique such as a restriction enzyme treatment, a PCR method, etc. Note here that filamentous fungi in the present invention denote filamentous fungi in a broad sense and it also includes yeast.

The present invention provides a vector in which the above-mentioned modified promoter is integrated. Such vectors can be used for producing a protein of interest. For example, an expression vector is constructed by introducing a structural gene of a protein of interest under control of the modified promoter. An appropriate host is transformed by using this, and the transformant in which a modified promoter and the structural gene of the protein of interest are appropriately introduced is cultured in conditions capable of producing the protein. Thereby, the protein of interest is collected from the culture medium or fungus body. Note here that the vector in which the modified promoter is integrated used in the present invention includes a vector in which a structural gene of a specific protein is integrated under control of the modified promoter.

It is preferable that the vector of the present invention has a selection marker suitable for selecting the transformant when filamentous fungi as a host are transformed. As a selection marker, an appropriate selection maker can be employed depending on the host to be used. Examples of the selection marker includes an auxotrophic complementary gene such as ornithine carbamoyltransferase gene (argB), nitrate reduction enzyme gene (niaD), acetamidase gene (amdS), tryptophan synthase gene (trpC), dihydrofolate reductase gene (DHFR), etc., and drug resistant gene against oligomycin, destomycin, hygromycin, etc.

As a host for producing proteins, filamentous fungi classified into genus *Aspergillus* (*Aspergillus oryzae*, *Aspergillus niger*, *Aspergillus nidulans*), genus *Penicillium*, genus *Trichoderma*, genus *Rhizopus*, etc. can be used. Preferably, filamentous fungi of genus *Aspergillus* is used. Among them, from the viewpoint of safety, *Aspergillus oryzae* or niger is preferably used.

In order to examine whether not only a protein originally produced by filamentous fungi in which a modified promoter is to be introduced (homogeneous protein) but also a protein that is not originally produced by filamentous fungi in which a modified promoter is to be introduced, that is to say, a protein that is produced for the first time by the exogenous insertion of a gene encoding a protein (heterogeneous protein) can be expressed efficiently or not, the present inventors have produced a transformant obtained by inserting an amylase gene of *Aspergillus oryzae* into *Aspergillus oryzae* as a host, and further transformant of laccase gene, which is much different from *Aspergillus oryzae* in terms of phylogenetic systematics, and confirmed the expression of proteins.

The proteins that can be produced by using the modified promoter of the present invention are not particularly limited. Examples include sugar-related enzyme such as a-amylase, glucoamylase, a-glucosidase, cellulase, pectinase, etc.; oxidation-reduction enzyme such as laccase, peroxidase, etc.; protease such as chymosin; lipase, and the like. The protein may be homogeneous protein or may be a heterogeneous protein.

The introduction of the vector of the present invention into a host can be carried out by a conventional method. For example, it can be carried out by the method by Turner et al. using, for example, fungus body as a protoplast (see Gene, 36, 321-331 (1985)). Besides, the method by Gomi et al. (Agric. Biol. Chem., 51,323-328 (1987)) may be employed.

The transformant in which the modified promoter of the present invention and the structural gene of a protein of interest are appropriately inserted is cultured in conditions capable of expressing the structural gene. Thereby, the protein of interest can be produced. As a culture medium, an appropriate one can be used depending upon the host to be used. For example, various media which are commercially available or medium which is obtained by adding to one of these media components such as arginine, uridine, which are necessary for development, selection and promoting expression of proteins can be used.

The protein of interest can be collected from the culture medium or fungus body after desirable time of culture. That is to say, if the protein is a secretory protein, the proteins can be collected from the culture medium, and if the protein is other than the secretary protein, they can be collected from the fungus body. When the proteins are collected from the culture medium, the protein of interest can be obtained as follows. For example, the culture supernatant is filtrated and centrifuged, so that impurities are removed. Then, separation and purification is carried out by employing the combination of salting out such as an ammonium sulfate precipitation, dialysis, various chromatographies, and the like. On the other hand, when the proteins of interest are collected from the fungus body, for example, fungus body is disrupted by compression process, ultrasonic process, etc. Then, separation and purification are carried out by the same method as mentioned above, and thereby the proteins of interest can be obtained. Note here that the above-mentioned series of processes (disrupting the fungus body, separation and purification) may be carried out after previously collecting the fungus body by filtration, centrifugation, etc.

Hereinafter, the present invention is described more specifically using Examples. However, the present invention is not limited to these Examples alone. In Examples, unless otherwise notified, for restriction enzymes and other enzymes for gene manipulation, products by Takara Shuzo Co., Ltd. or Toyobo Co., Ltd. were used. Note here that the reaction of enzymes is carried out under the conditions specified in instructions attached to each product.

Furthermore, as a synthetic oligo DNA used in Examples, those synthesized in Takara Shuzo Co., Ltd. or Invitorogen Japan K.K. were used. The sequence determination was performed with ABI PRISM 310 Genetic Analyzer (Applied Biosystems), and a PCR reaction was carried out by using Thermal Cycler (PerkinElmer Japan Co., Ltd.).

EXAMPLE 1

Subcloning of Promoter Region

By using pTG-taa [Mol. Gene. Genet., 254, 119-126 (1997)] including 3164 bp of a Taka-amylase A gene (taaG2) of an *Aspergillus oryzae* strain JCM02239 [Gene, 84, 319-327 (1989)] as a starting material, a Taka-amylase A gene promoter region and a coding region of Taka-amylase A gene were prepared.

Firstly, from pTG-taa, 750bp of EcoRI-SalI fragment including a Taka-amylase A (taaG2) promoter region was obtained. This fragment was inserted into an EcoRI-SalI site of a multicloning site of a plasmid pKF18K (Toyobo Co., Ltd.) to obtain a plasmid pKF-taaP including a Taka-amylase promoter. Introducing mutation into a promoter region and the construction of the modified promoter region were carried out using this plasmid.

EXAMPLE 2

Obtaining DNA Fragment Including Binding Sequence of Transcriptional Regulation Factor A fragment including a CCAAT sequence [Mol. Gen. Genet., 237, 251-260(1993)] that is a binding factor of a previously reported wide-domain transcription activation factor (HAP) and SRE [Mol. Gen. Genet., 262, 668-676 (1999)] that is a binding factor of transcription activation factor of starch degrading enzyme gene cluster (AmyR) was obtained as follows.

Firstly, as a synthetic DNA in which an XhoI site was added to the 5'-end side and a NotI site was added to the 3'-end side of a CCAAT sequence, XNF (5'-CCGCTCGAGGCAC-CATCCAATTAGAAGCGCGGCCGCTAAACTAT3': SEQ ID NO: 13), and as a complementary strand of this sequence, XNR (5'-ATAGTTTAGCGGCCGCGCTTCTAATTG-GATGGTGCCTCGAGCGG-3': SEQ ID NO: 14) were synthesized. Then, complementary strands of the synthetic DNAs were mixed with each other and heated at 98° C. for 10 minutes, then cooled down to 30° C. over two hours, and then cooled down to 4° C. for annealing. Thereby, a DNA fragment including a CCAAT sequence singly was obtained.

On the other hand, as a synthetic DNA in which an SpeI site was added to the 5'-end side and HincII was added to the 3'-end side, SREf (5'-GACTAGTTAACCTAGGGGCG-GAAATTTAACGGGATGTTAACTAGTC-3': SEQ ID NO: 15) and as a complementary strand of this sequence, SREr (5'-GACTAGTTAACATCCCGTTAAATTTC-CGCCCCTAGGTTAACTAGTC-3: SEQ ID NO: 16) were synthesized, and a DNA fragment including SRE singly was obtained by the same method as mentioned above. Hereinafter, a DNA fragment including only the CCAAT sequence prepared herein will be referred to as a "CCAAT fragment" and a DNA fragment including only SRE will be referred to as a "SRE fragment."

Then, a DNA fragment including the region from the CCAAT sequence to the SRE (SEQ ID NO: 9, hereinafter, referred to as a "CCAAT-SRE fragment") was obtained by carrying out 30 cycles of PCR reactions using the following primers and pKF-taaP as a template prepared in Example 1. Each cycle consists of 94° C. for 30 seconds; 54° C. for 30 seconds; and 72° C. for 90 seconds. Note here that two kinds of fragments, i.e., a fragment including a PstI site (SEQ ID NO: 10, hereinafter, which will be referred to as a "CCAAT-SRE (PstI) fragment") and a fragment including an XhoI-NotI site (SEQ ID NO: 11, hereinafter, which will be referred to as a "CCAAT-SRE (XhoI-NotI) fragment") were prepared.

Upstream primer with PstI site added (SEQ ID NO: 17)
CSPf:   5'-AAACTGCAGACCACCTCTAGGCATCGGACG-3'

Downstream primer with PstI site added (SEQ ID NO: 18)
CSPr:   5'-TTTCTGCAGTGTTGATTTGTGGTTGAGTGG-3'

Upstream primer with XhoI site added (SEQ ID NO: 19)
CSXf:   5'-CGGCTCGAGGCATCGGACGCACCATCC-3'

Downstream primer with NotI added (SEQ ID NO: 20)
CSNr:
5'-ATAGTTTAGCGGCCGCCGACTGTGATTTGTGGTTGAGTGG-3'

EXAMPLE 3

Construction of Plasmid Including Modified Promoter

Introduction of mutation into a promoter region of a Taka-amylase A gene was carried out as follows. Firstly, in order to introduce a restriction enzyme site for modifying a promoter region into pKF-taaP prepared in Example 1, site-directed mutation was introduced into pKF-taaP using the below-mentioned primers and Mutan-Super Express Km Kit (TAKARA). Note here that FIG. 1 shows a sequence (SEQ ID NO: 12) of a wild type promoter; and FIG. 2 shows the position of the introduced restriction enzyme.

Primer for introducing NotI site into a down stream region (position 465 where a Taka-amylase promoter shown in SEQ ID NO: 12 is located)

Not-b:                                                        (SEQ ID NO: 21)
5'-CGCTTGGATTCCCCGCCCGCGGCCGCAGAGCTTAAAGTATGTCCC-3'

Primer for introducing XhoI site into a downstream region (position 440 where a Taka-amylase promoter shown in SEQ ID NO: 12 is located)

Xho-b:                                                        (SEQ ID NO: 22)
5'-GAATGCAATTTAAACTCTTCCTCGAGTCGCTTGGATTCCCCGCCC-3'

Primer for introducing NotI site into an upstream region (position 153 where a Taka-amylase promoter shown in SEQ ID NO: 12 is located)

Not-a:                                                        (SEQ ID NO: 23)
5'-GTAGTAAAACCCCGGAGTCAGCGGCCGCCAAGCCCAAGTCCTTCACG-3'

Primer for introducing XhoI site into an upstream region (position at 128 where a Taka-amylase promoter shown in SEQ ID NO: 12 is located)

Xho-a:                                                        (SEQ ID NO: 24)
5'-CGTCAAGGGATGCAAGACTCGAGTAGTAAAACCCCGGAGTC-3'

Primer for introducing NotI site into a region between the CCAAT sequence and SRE (position 252 where a Taka-amylase promoter shown in SEQ ID NO: 12 is located)

Not:                                                          (SEQ ID NO: 25)
5'-GCACCATCCAATTAGAAGCGCGGCCGCGAAACAGCCCAAGAAAAAGG-3'

Primer for introducing SpeI site into a downstream region (position 490 where a Taka-amylase promoter shown in SEQ ID NO: 12 is located)

(SEQ ID NO: 26)
STATA:    5'-TAAAGTATGTCACTAGTCGATGCGAT-3'

Next, a CCAAT fragment prepared in Example 2 was cut with XhoI and NotI and recovered and purified by agarose gel electrophoresis. The obtained DNA fragment was inserted into an XhoI-NotI site introduced into a downstream region of the promoter as mentioned above and a plasmid pKF-CCAATb including a modified promoter PCCAATb was produced. Similarly, a plasmid pKF-SREb including a modified promoter PSREb in which a DNA fragment, obtained by cutting an SRE fragment prepared in Example 2 with HincII, was inserted into an XhoI-NotI site at the downstream region of the promoter; a plasmid pKF-PCSP including a modified promoter PCSP in which a DNA fragment, obtained by cutting a CCAAT-SRE (PstI) fragment prepared in Example 2 with PstI, was inserted into a PstI site at the downstream region of the promoter; and a plasmid pKF-PCSb including a modified promoter PCSb in which a DNA fragment, obtained by a CCAAT-SRE (XboI-NotI) fragment prepared in Example 2 with XhoI and NotI, was inserted into an XhoI-NotI site at the downstream region of the promoter were produced respectively. Furthermore, a CCAAT-SRE (XhoI-NotI) fragment was cut with XhoI and NotI, and recovered and purified. The recovered and purified fragment was inserted into an XhoI-NotI site at the downstream region of the promoter, and then a CCAAT-SRE (PstI) fragment was inserted into a PstI site, and thereby a plasmid pKF-PCSPb including a modified promoter PCSPb in which CCAAT-SRE fragments were inserted into two positions was produced.

EXAMPLE 4

Construction of Plasmid for Evaluating Promoter Activity

Figure 3:
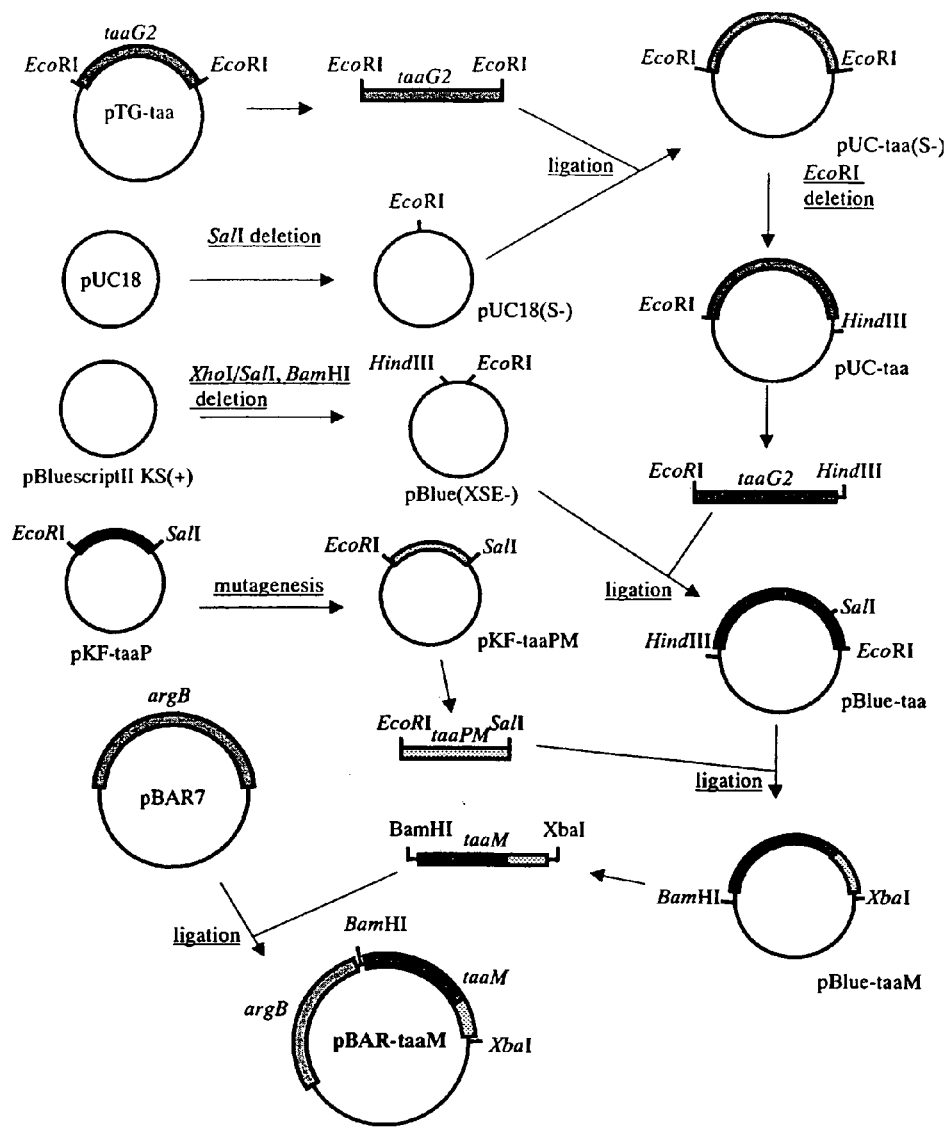
FIG. 3 shows a process of constructing a plasmid for evaluating a promoter activity in Example 4.

FIG. 3 shows a process for producing a plasmid for evaluating a promoter activity. Firstly, after a plasmid pUC18 (Toyobo Co., Ltd.) was digested with SalI, it was subjected to Klenow treatment so as to have blunt ends and subjected to self-ligation, thereby obtaining a plasmid pUC18 (S–) with deletion of a SalI site. On the other hand, an EcoRI fragment of a Taka-amylase A gene was isolated from the plasmid pTG-taa. This fragment was inserted into an EcoRI site of multicloning site of the pUC18 (S–) so as to obtain a pUC-taa(S–). This plasmid pUC-taa(S–)was partially degraded by EcoRI and a plasmid pUC-taa with deletion of an EcoRI site at the 3'-end side of taaG2 gene was obtained. Similarly, a plasmid pBlue (XSE–) with deletion of XhoI, SalI, BamHI from pBluescriptII KS(+) was obtained.

Then, an EcoRI-HindIII fragment including taaG2 was isolated from pUC-taa and this fragment was inserted into an EcoRI-HindIII site of multicloning site of a plasmid pBlue (XSE–), and thus a plasmid pBlue-taa including taaG2 was obtained.

Then, from plasmid pKF-taaPM series (pKF-CCAATb, pKF-SREb, pKF-PCSP, pKF-PCSb or pKF-PCSPb) including the modified promoter region obtained in Example 3, an EcoRI-SalI fragment of the modified promoter region was isolated; inserted into a multicloning site EcoRI-SalI of a plasmid pBlue-taa, and then a plasmid pBlue-taaM in which the modified promoter region and taaG2 gene were ligated with each other was obtained. From pBlue-taaM, XbaI-BamHI fragment of taaG2 gene including the modified promoter was isolated, and integrated into a multicloning site XbaI-BamHI of a plasmid pBAR7 (plasmid in which argB gene with deletion of C-end derived from *Aspergillus nidulans* was inserted into pBluescriptII KS(+)) so as to obtain plasmid pBAR-taaM series (pBAR-CCAATb, pBAR-SREb, pBAR-PCSP, pBAR-PCSb and pBAR-PCSPb) for measuring promoter activity.

EXAMPLE 5

Obtaining Transformant Having Modified Promoter

1. Transformation

Transformation of filamentous fungi was carried out as follows. Firstly, each plasmid of the pBAR-taaM series (pBAR-CCAATb, pBAR-SREb, pBAR-PCSP, pBAR-PCSb and pBAR-PCSPb) obtained in Example 4 was digested with EcoRV, followed by purification with phenol/chloroform extraction and ethanol precipitation. Then, the purified product was used for transformation.

Then, *Aspergillus nidulans* was transformed with these plasmids. *Aspergillus nidulans* strain ABPU1 (biA1; pyrG89; wA3; argB2; pyroA4) with deletion of ornithine carbamoyl transferase gene was cultured with shaking in a medium obtained by adding necessary nutrient (arginine, uridine, pyridoxine and biotin) to a complete medium (2% malt extract, 2% glucose and 0.1% Bacto-pepton) at 37° C. over night. Then, the obtained fungus bodies were suspended in a cell wall digesting solution [20 mg/ml Yatalase (Takara Shuzo Co., Ltd.), 0.8 M NaCl, 10 mM phosphate buffer (pH6.0)] and shaken mildly at 30° C. for 1 to 2 hours to form a protoplast. The obtained protoplast was filtered with nylon filter, thereby removing residual fungus bodies. Then, by using this protoplast, preparation and transformation of competent cell were carried out in accordance with the method by Turner et al. [Gene, 36, 321-331(1985)], and 20 to 40 strains per plasmid of trnasformants capable of growing in a medium without containing arginine (Czapek-Dox agar medium (0.2% NaNO$_3$, 0.1% K$_2$HPO$_4$, 0.05% KCl, 0.05% MgSO$_4$.7H$_2$O, 2% glucose (pH5.5)) to which uridine, pyridoxine and biotin were added) were obtained.

2. Selection of Transformant by Southern Blotting Analysis

From each transformed strain, a chromosomal DNA was prepared as follows. Firstly, the transformed strain was cultured with shaking in a complete medium to which necessary nutrient (uridine, pyridoxine and biotin) was added at 37° C. over night so as to obtain fungus bodies. Then, the obtained fungus bodies were collected and washed by using a Buchner funnel and filter paper No. 2 (Advantech) and washed with sterile water. After removing excess water, frozen at −80° C. and lyophilized by using FREEZONE (LABCONCO). After drying, 1 mm glass beads were added and disrupted with a Multi-Beads Shocker (Yasui KikaiCo.,) at 2000 rpm for 5 minutes to obtain pulverized powder. To the disrupted fungus bodies, an extraction solution [1% hexadecylmethyl ammonium bromide, 0.7M NaCl, 50 mM Tris-HCl, 10 mM EDTA, 1% β-mercaptoethanol] was added and stirred and thereafter left it at room temperature for 30 minutes. The obtained lysate was subjected to phenol/chloroform extraction and contaminated proteins were removed, followed by adding an equal amount of isopropanol precipitate DNA. This precipitates were dissolved in a TE solution containing 0.1 mg/ml RNase and reacted at 37° C. for 30 minutes. Furthermore, a TE solution containing 0.2 mg/ml proteinaseK was added and reacted at 37° C. for 30 minutes. This solution was subjected to phenol/chloroform extraction and precipitated in 2.5 volume of cold ethanol. This precipitate was rinsed with 70% ethanol and dried, followed by dissolving it in a TE solution, which was defined as a chromosomal DNA solution.

Southern blotting analysis includes: digesting a chromosomal DNA with PvuII or EcoRV, then separating it by agarose gel electrophoresis to blot on nylon membrane (Roche). Thereafter, detection was carried out using about 1000 bp of BglII-SmaI digested product of taaG2 as a probe. At this time, labeling of probe and detection of signals were carried out using DIG nucleic acid detection kit (Roche).

From the result of Southern blotting analysis, arbitrarily two or more transformants, i.e., transformant that is transformed strain in which one copy of plasmid is integrated into an argB locus homologously and is capable of measuring the promoter activity without being affected by the position when it is integrated into, the chromosome and by the number of copies of the gene to be inserted were selected.

EXAMPLE 6

Measurement of Amylase Activity of Transformant and Evaluation of Modified Promoter By using a transformant obtained in Example 5, in which pBAR-CCAATb or pBAR-SREb was integrated, the change in the promoter activity, when the modification by inserting a CCAAT sequence or SRE singly was carried out, was evaluated. Furthermore, by using a transformant in which pBAR-PCSP was integrated, the case where both CCAAT sequence and SRE were inserted at the same time was similarly evaluated. Firstly, each transformant was inoculated radially on an agar medium obtained by adding necessary nutrient (uridine, pyridoxine and biotin) to a minimum medium (0.9% NaNO$_3$, 0.05% KCl, 0.05% KH$_2$PO$_4$, 0.15% Trace element, 0.05% MgSO$_4$.7H$_2$O, 1% glucose (pH6.5)), and cultured at 37° C. for three days. Thereafter, from this agar medium, conidiospores were suspended in a solution for suspending spores (0.01% tween80, 0.8% NaCl) and filtrated with cotton and a spore suspension solution was prepared. From this spore suspension solution, 1×10$^8$ conidiospores were inoculated on 100 ml of medium obtained by adding necessary nutrient other than arginine (that is, uridine, pyridoxine and biotin) to a SP medium (1% Starch, 1% polypeptone, 0.5% KH$_2$PO$_4$, 0.1% NaNO$_3$, 0.05% MgSO$_4$.7H$_2$O (pH6.5)), cultured with shaking at 37° C. for 36 hours, and then fungus bodies and supernatant were separated from each other by using a Buchner funnel and a filter paper. The supernatant was defined as an enzyme solution.

Amylase activity was quantified by: preparing 150 μl of reaction system by adding an enzyme solution to 20 mM sodium acetate buffer, 10 mM CaCl$_2$, and 2% Soluble Starch (Nacalai Tesque Inc.); reacting this reaction system at 37° C. for 20 minutes to generate reduction sugar; and quantifying the generated reduction sugar by Nelson-Somogyi method. Furthermore, the amount of enzymes for releasing 1 μmol/min of glucose was represented by 1 unit. By employing the amylase activity measured as mentioned above as an index, the promoter activities of the wild type promoter and the modified promoter were evaluated.

Figure 4:
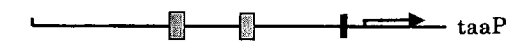
FIG. 4 is a table summarizing measurement results of the amylase activities measured in Example 6. Left to the table, an insertion position of a CCAAT sequence or SRE in each modified promoter are schematically shown. A dotted box shows an inserted fragment. taaP denotes a wild type promoter; PCCAATb denotes a modified promoter into which a CCAAT sequence is inserted; PSREb denotes a modified promoter into which SRE is inserted; PCSP denotes a modified promoter into which a CCAAT-SRE fragment is inserted, respectively.

FIG. 4 shows a measurement result of the amylase activity. As is apparent from this Table, when the modified promoters (PCCAATb and PSREb) in which CCAAT sequence or SRE was inserted were compared with the wild type promoter (taaP), the activity was deteriorated or was not substantially different from each other. Thus, the effect of enhancing the promoter activity by singly inserting CCAAT sequence or SRE was not observed. Furthermore, also when a plurality of these fragments were inserted, similarly, the effect of enhancing the promoter activity was not observed (data are not shown). From these results, it was thought that the promoter had been already optimized, and the adverse effect on the structure of promoter due to the introduction of mutation was manifested more significantly than the effect obtained by inserting the CCAAT sequence or SRE.

On the other hand, in the modified promoter (PCSP) in which a CCAAT sequence and SRE were inserted at the same time, as compared with the wild type promoter (taap), significant increase in the activity was observed, and about 4 times amylase activity was observed. From the results, it can be said that in order to increase the promoter activity, it is important to insert both CCAAT sequence and SRE at the same time.

EXAMPLE 7

Effect of Modification of Promoter by Inserting a Plurality of CCAAT Sequences and SREs Then, the effect of increasing the amount of production of amylase when the promoters in which one copy, two copies and three copies of CCAAT-SRE fragments were respectively inserted into a promoter region was investigated. In order to investigate the effect on the promoter activity when at most three CCAAT-SRE fragments were inserted into the promoter region (original 1+inserts 3=4), a plasmid pKF-PCSPPb in which CCAAT-SRE (PstI) fragment (SEQ ID NO: 10) obtained in Example 2 was inserted into a PstI site of pKF- PCSPb obtained in Example 3 was prepared. By using this plasmid, a plasmid pBAR-CSPPb for measuring the promoter activity was prepared as in Example 4, and a transformant in which pBAR-CSPPb was integrated in accordance with Example 5 was obtained. As to this transformant, the same as in Example 6, a spore suspension solution was prepared. From this spore suspension solution, $1 \times 10^8$ conidiospores were inoculated on 100 ml of medium obtained by adding necessary nutrient other than arginine (uridine, pyridoxine and biotin) to a SP medium (1% Starch, 1% polypeptone, 0.5% $KH_2PO_4$, 0.1% $NaNO_3$, 0.05% $MgSO_4.7H_2O$ (pH6.5)), cultured with shaking at 37° C. for 40 hours, and then the amylase activity was measured in accordance with Example 6. For comparison, the amylase activities of a transformant in which a plasmid pBAR-taa having a wild type promoter was integrated; a transformant in which a plasmid pBAR-CSb having a promoter modified by inserting one CCAAT-SRE fragment; and a transformant in which a plasmid pBAR-CSPb having a promoter modified by inserting two CCAAT-SRE fragments were also measured.

Figure 5:
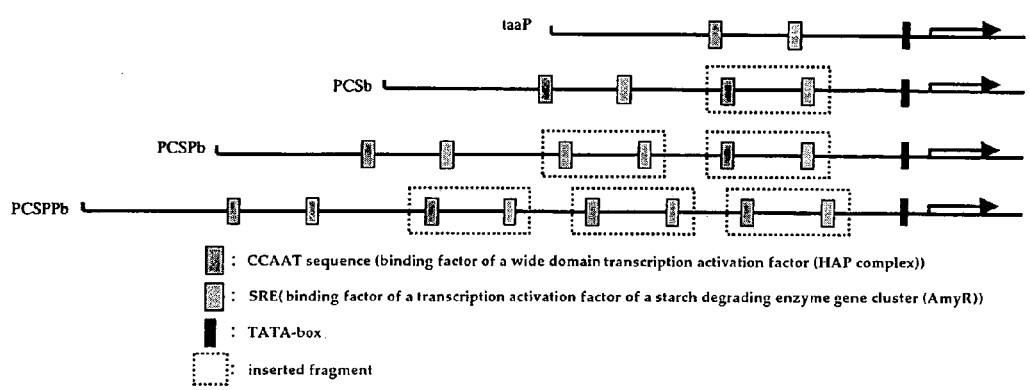
FIG. 5 is a table summarizing amylase activities measured in Examples 7 and 8. In the upper part, the insertion position of the CCAAT-SRE fragment in each modified promoter is schematically shown. A dotted box shows an inserted fragment. taaP denotes a wild type promoter; PCSb and PCSP denotes a modified promoter into which one CAAT-SRE fragment is inserted; PCSPb denotes a modified promoter into which two CCAAT-SRE fragments are inserted; and PCSPPb denotes a modified promoter into which three CCAAT-SRE fragments are inserted, respectively.

The measurement results are shown in Table (column of starch) of FIG. 5. Note here that upper part of this FIG. 5, the positions in which a CCAAT sequence or SRE is inserted in each modified promoter is schematically shown. As is apparent from this Table, every time a region from the CCAAT sequence to the SRE is inserted, the increase in the production amount of amylase was observed. That is to say, by inserting a plurality of CCAAT-SRE fragments, it was confirmed that it was possible to improve the production amount of amylase.

EXAMPLE 8

Effect of Modified Promoter on Carbon Source

In order to investigate the effect of reducing catabolite repression for glucose by modified promoters PCSb, PCSPb and PCSPPb in which one copy, two copies and three copies of CCAAT-SRE fragments were inserted, the amylase activities when a transformant in which pBAR-CSb was integrated, a transformant in which pBAR-CSPb was integrated and a transformant pBAR-CSPPb was integrated were cultured in a GP medium whose C source was glucose (1% Glucose, 1% polypeptone, 0.5% $KH_2PO_4$, 0.1% $NaNO_3$, 0.05% $MgSO_4.7H_2O$ (pH6.5)) were measured, and compared with the amylase activity (Example 7) when culturing was carried out in the SP medium whose C source was starch (1% Starch, 1% polypeptone, 0.5% $KH_2PO_4$, 0.1% $NaNO_3$, 0.05% $MgSO_4.7H_2O$ (pH6.5)).

The measurement results when the C source was glucose are shown in Table (column of glucose) of FIG. 5. The production amount of amylase when a transformed strain having a wild type promoter is cultured in a medium using glucose as a C source is about one-fourteenth of the production amount of amylase when a transformed strain having a wild type promoter is cultured in a medium using starch as a C source. On the other hand, in the transformed strain having a modified promoter, the ratio of the production of amylase when being cultured in a medium using glucose as a C source to the production amount of amylase when being cultured in a medium using starch as a C source is about 1:8. These results showed that the modified promoter in which a CCAAT-SRE fragment was inserted into the promoter region had an effect of reducing catabolite repression as compared with a wild type promoter. Furthermore, also in the case where the culturing was carried out in a medium using glucose as a C source, similar to the case where culturing was carried out in a medium using starch as a C source, the effect of enhancing the expression by the insertion of a plurality of the CCAAT-SRE sequences is observed, it was shown that by using the modified promoter, two effects, that is, the effect of enhancing the expression and the effect of reducing the catabolite repression were obtained. That is to say, it was determined that when a modified promoter in which a plurality of CCAAT-SRE sequences are integrated was used, even if the carbon source was glucose, amylase could be produced excellently.

EXAMPLE 9

Investigation of Diversity of DNA Fragment Having Enhancer Function

It was investigated whether or not the effect of enhancing the promoter activity was maintained when a part of SRE portion of the CCAAT-SRE fragment was changed. Firstly, by using the following primer MSRE designed so that the SRE part was substituted from a wild type (CGGAAATT-TAAAGG: SEQ ID NO: 6) to (CGGAATTTAAACGG: SEQ ID NO: 7) and Mutan-Super Express Km Kit (TAKARA), a site-directed mutation was introduced into pKF-taaP. From the mutated promoter region, a CCAAT-SRE (XhoI-NotI) fragment was obtained and this was defined as a CCAAT-mSRE fragment. Then, by the same method as in Examples 2 and 3, a modified promoter PCmSb in which a CCAAT-mSRE fragment into an XhoI-NotI site at the downstream region of the promoter, and a plasmid pKF-PCmSb including this modified promoter was used and a plasmid pBAR-CmSb for measuring the amylase activity was constructed by the same method as in Example 4. Then, the promoter activity was evaluated by the same method as in Examples 5 and 6.

Primer for substituting a part of the SRE portion with other base MSRE: 5'-TAGGGGCGGAATTTAAACGGGATTAA-3' (SEQ ID NO: 27)

The measurement results of the amylase activities are shown in Table of FIG. 6. As is apparent from this table, the promoter (PCmSb) provided with base substitution exhibited about 3.2 times larger expression amount than that by a wild type (taaP) and exhibited the same effect of enhancing the promoter activity as that of a promoter (PCSb) in which base substitution was not provided in SRE. From this results, it was confirmed that even if a part of the sequence in the SRE portion was mutated, the effect of increasing the promoter activity, that is, the enhancer function could be maintained.

EXAMPLE 10

Investigation of Insertion Position of Enhancer Sequence

Promoters were modified by varying the insertion position of a CCAAT-SRE fragment. The influence of the insertion position on the promoter activity was compared and the effective insertion position was investigated.

Firstly, by the same method as in Example 3, modified promoters PCmSa, PCmSN and PCmSS in which the CCAAT-mSRE fragment prepared in Example 9 was respectively inserted into an XhoI-NotI site at the upstream region of the promoter, a NotI site in a region between the CCAAT sequence and the SRE, or a SpeI at the downstream region were prepared. By the same method as in Examples 3 and 4, plasmids including these modified promoters for measuring the amylase activity were constructed. Then, by the same method as in Examples 5 and 6, the promoter activities were compared.

The measurement results of the amylase activity are shown in Table of FIG. 6. Note here that on the left part of the table, the insertion position of the CCAAT-mSRE fragment in each modified promoter is schematically shown. As is apparent from this Table, in the modified promoter PCmSN in which a region including from the CCAAT sequence to SRE was inserted between the originally existing CCAAT sequence and SRE, the increase in the promoter activity was not observed but when it was inserted into any regions other than the position between the CCAAT sequence and SRE, the increase in the expression amount of amylase was observed. However, the amount of amylase expression by using the promoter PCmSb (Example 9) whose insertion position was in an XhoI-NotI site at the downstream region of the promoter was larger than those of the modified promoters PCmSa and PCmSS whose insertion position was upstream to the CCAAT sequence or just before the TATA-box. This suggested that the most suitable insertion position of the CCAAT-mSRE fragment was at the downstream region to the originally existing SRE and that the distance between the transcription start point and the CCAAT-mSRE fragment was not correlated to the promoter activity. Note here that it is thought that the same as true in the CCAAT-SRE fragment.

EXAMPLE 11

Obtaining High Production Strain of Amylase

By using an amylase gene having a modified promoter, an *Aspergillus nidulans* strain capable of producing amylase with high productivity was tried to be obtained.

From the transformant prepared in Examples 5 or 7, strains (CSb16, CSP6, and SPb19) in which multiple copies of amylase gene having a modified promoter were integrated into an argB locus homologously were selected and cultured on 100 ml of SPY medium (3% Starch, 0.2% KCl, 0.1% $KH_2PO_4$, 0.05% $MgSO_4.7H_2O$, 1% polypeptone, and 0.5% Yeast Extract) at 37° for 5 days and the amylase activity was measured by the method shown in Example 6. The results are shown in table of FIG. 7. As compared with a taa2 strain having a wild type promoter, a CSb17 strain having a modified promoter exhibited 5 times expression amount of amylase. In the strain in which multiple copies of amylase genes were integrated, in accordance with the increase in the number of copies, the expression amount tends to increase. The strain with the highest expression amount had about 34 times as the expression amount of a wild type promoter and expressed about not less than 10 gram/litter of amylase when represented by a mass of proteins. It could be confirmed from this results that by intengrating multiple copies of amylase genes having a modified promoter, a large amount of proteins was able to be produced.

EXAMPLE 12

Comparison of Productivity of Amylase Depending upon the Difference in Carbon Sources Next, by using a CSP6 strain having two CCAAT-SRE fragments in a promoter region and a CSPb19 strain having three CCAAT-SRE fragments in a promoter region, the difference in the expression amount with respect to various C source was examined.

The CSP6 strain and the CSPb19 strain were cultured in 100 ml of SPY medium (C source: starch: 3% Starch, 0.2% KCl, 0.1% $KH_2PO_4$, 0.05% $MgSO_4.7H_2O$, 1% polypeptone, 0.5% Yeast Extract), MPY medium (C source; maltose: 3% Maltose, 0.2% KCl, 0.1% $KH_2PO_4$, 0.05% $MgSO_4.7H_2O$, 1% polypeptone, 0.5% Yeast Extract), and GPY medium (C source: glucose: 3% Glucose, 0.2% KCl, 0.1% $KH_2PO_4$, 0.05% $MgSO_4.7H_2O$, 1% polypeptone, 0.5% Yeast Extract) at 37° for 5 days, and then the amylase activity was measured by the same method as in Example 6.

The measurement results are shown in Table of FIG. 8. As is apparent from this table, in both strains, strains cultured using maltose as a C source showed lower amylase activity than strains cultured using starch as a C source. This is thought to be because the amylase activity was influenced by, for example, depletion of C source due to the use of low molecule as a C source. Furthermore, when glucose was used as a C source, in the CSP6 strain, the expression amount was significantly lowered by the catabolite repression. On the other hand, the CSPb19 strain maintained substantially the same expression amount as the case where starch was used as a C source. It could be confirmed from this results that when a transformant in which multiple copies of plasmids were introduced was cultured for a long time, the catabolite repression effect or the effect of enhancing the expression amount were manifested more significantly. That is to say, it was confirmed that in a case where multiple copies of plasmids were introduced for the purpose of obtaining a strain capable of producing amylase with higher productivity, by using a modified promoter having three or more CCAAT-SRE sequences, it was possible to obtain a strain capable of producing amylase with higher productivity.

EXAMPLE 13

Effect of the Change in Distance between CCAAT and SRE

In the CCAAT-SRE fragment, by changing the distance between CCAAT and SRE and the influence of the distance on the enhancer function was investigated.

Firstly, a PCR reaction was carried out by using primers CSXf and CSNr shown in Example 2 and primers CBglr and SBglf shown below, and a fragment including a CCAAT sequence and a fragment including SRE were obtained separately. These fragments were linked at a BglII site, and thereby a DNA fragment having a short distance between the CCAAT sequence and the SRE (hereinafter, which will be referred to as "sCCAAT-mSRE fragment") was obtained and inserted into an XhoI-NotI site at the downstream region of the promoter (taap) region so as to produce a modified promoter PsCmSb. By using this modified promoter, the promoter activity was evaluated by the same method as in Examples 3 to 6.

Downstream primer with BglII site added

```
                                        (SEQ ID NO: 28)
    CBglr:    5'-GAAGATCTCTGTTTCGCTTTGCTGCTTC-3'
```

Upstream primer with BglII site added

```
                                        (SEQ ID NO: 29)
    SBglf:    5'-GAAGATCTTCCAGAGTGACTAGGGGCGG-3'
```

The measurement results of the amylase activity are shown in Table of FIG. 9. As shown in this table, the promoter (PsCmSb) that was modified by using sCCAAT-SRE fragment showed about 1.6 times effect of increasing the expression amount of amylase as compared with a wild type promoter (taaP). That is to say, also when the distance between the CCAAT sequence and the SRE is shortened, the effect of enhancing the promoter activity can be obtained. This strongly suggests that two regions, CCAAT sequence and SRE are responsible for the activation of promoter. Note here that PsCmSb has increasing effect that is only a half as compared with PCmSb in which the original size of CCAAT-mSRE region was inserted, but the reduction of increasing effect is thought to be because the positional relationship between a HAP complex linked to the CCAAT sequence and AmyR liked to the SRE is displaced from the optimal potion due to the change in the distance between the CCAAT sequence and SRE. That is to say, it is thought that by optimizing the distance between the CCAAT sequence and SRE, it was sufficiently possible to maintain the effect of enhancing the promoter activity possessed by the CCAAT-SRE fragment even when a shorter DNA fragment is used.

EXAMPLE 14

Investigation of Diversity of Enhancer Sequence (SRE)

When various mutations were introduced into a SRE portion of a wild type promoter (taap), the influence of the introduction of mutation on the promoter activity was examined. Firstly, by a PCR reaction using the below mentioned primers, modified promoters taaS (sequence in a SRE portion is CGGAAATTTAACGG: SEQ ID NO:8) and MSRE2 (sequence in a SRE portion is CGGAAATTTAATTA: SEQ ID NO: 30) in which a part of the bases of SRE existing in a wild type promoter (taap) were substituted were produced. By using these modified promoters, by the same method as in Examples 3 to 6, the promoter activity was evaluated.

```
                                            (SEQ ID NO: 31)
SREc (for taaS): 5'-GGGGCGGAAATTTAACGGGATTAATTTCC-3'

(SEQ ID NO: 32)
MSRE2 (for       5'-CGGAAATTTAATTAGATTAATTTCC-3'
MSRE2):
```

Figure 10:
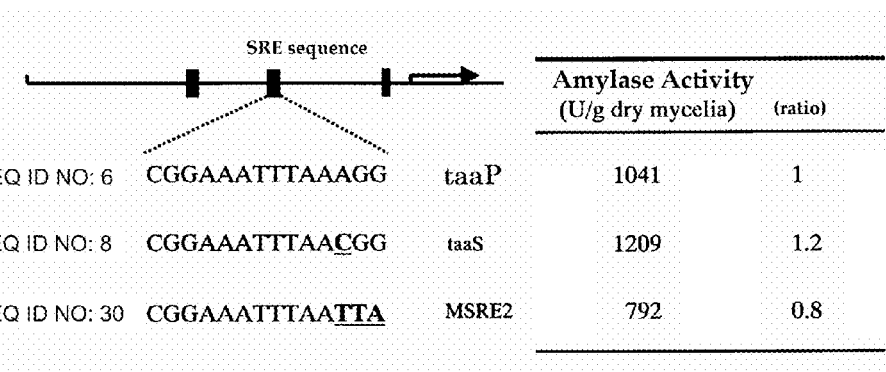
FIG. 10 is a table summarizing amylase activities measured in Example 14. Left to the table, a sequence of SRE region in each modified promoter is shown. taaP denotes a wild type promoter. In taaS, a base which is in the 12th position from the 5'-end side is substituted. Similarly, in MSRE2, bases which are in the 12th to 14th positions from the 5'-end side are substituted.

The measurement results of the amylase activity are shown in Table of FIG. 10. The modified promoter taaS in which the 12th base from the 5'-end side of SRE existing in a wild type promoter was substituted by C showed about 1.2 times greater amylase activity than that of the wild type promoter. It was determined from this result that even if the 12th base from the 5'-end side of SRE was mutated, the enhancer function possessed by SRE could be maintained, and that the sequence in which this base is substituted by C had more excellent function. On the other hand, in the modified promoter MSRE2 in which the 13th and 14th bases from the 5'-end side in the SRE portion are respectively substituted to T and A, the amount of expression of amylase was lowered to about 0.8 times of that of the wild type promoter. This results show that for maintaining the high enhancer function, not mutating the 13th and 14th bases from the 5'-end side in the SRE is important.

EXAMPLE 15

Construction of Plasmid for Expressing Amylase

In order to demonstrate that the use of a modified promoter is also effective in production system of enzymes using Aspergillus oryzae as a host, the following experiments were carried out using the modified promoters prepared in Example 3 and Example 7. Firstly, the plasmid pBAR-CSPb prepared in Example 4 was cut with XbaI and BamHI, and thereafter about 3600 bp of DNA fragments were recovered and purified by agarose gel electrophoresis. The recovered DNA fragment was inserted into the XbaI-BamHI cut site of a plasmid pYRG100 in which orotidine 5' phosphate decarboxylase gene (pyrG gene) was introduced, and thus a plasmid pYRG-CSPb for expression amylase gene was constructed. Note here that pYRG100 was produced as follows in accordance with the previous report (Nippon Shoyu Kenkyusyo Zasshi, 25(1), 21-26 (1999)). That is to say, a PCR reaction was carried out using a chromosomal DNA of *Aspergillus oryzae* strain AMA 1201 (FERM P-19089) as a template and using a primer PyrF and a primer PyrR mentioned below. The thus obtained amplified product was cut with SalI and HindIII to obtain a DNA fragment of about 1.9 Kbp, which was then inserted into SalI-HindIII of multicloning site of pUC119. Thus, pYRG100 was obtained.

```
                                            (SEQ ID NO: 33)
PyrF:    5'-TATGTCGACCCAAGCCGCTGCTGGAATTGA-3'

(SEQ ID NO: 34)
PyrR:    5'-GAAAAGCTTGATCAATACCGTACGGGAGAT-3'
```

EXAMPLE 16

Transformation of Strain Producing Amylase with Low Productivity (*Aspergillus Oryzae* Strain AMA 1201-P), and Strain Producing Amylase with High Productivity (Strain *Aspergillus Oryzae* KBN6217-56)

1. Transformation of *Aspergillus Oryzae*

By using a plasmid pYRG-CSPb prepared in Example 15, when the modified promoter was used within the same kinds of *Aspergillus oryzae* (*Aspergillus oryzae* was transformed with a gene of *Aspergillus oryzae*), the effect of improving the productivity of proteins was evaluated. Firstly, the transformation of *Aspergillus oryzae* by the plasmid pYRG-CSPb prepared in Example 15 was carried out as follows. *Aspergillus oryzae* strain AMA 1201-P that is a strain with deletion of pyrG gene and *Aspergillus oryzae* strain KBN 6217-56 that is a strain with deletion of the same gene were cultured with shaking in a complete medium (2% malt extract 2% glucose, and 0.1% Bacto-pepton) to which uridine was added at 30° C. over night. Then, the obtained fungus bodies were suspended in a cell wall digesting solution [20 mg/ml Yatalase (Takara Shuzo Co., Ltd.), 0.8 MNaCl, 10 mM phosphate buffer (pH6.0)] and shaken mildly at 30° C. for 1 to 2 hours to form a protoplast. The obtained protoplast was filtered with nylon filter, thereby removing the residual fungus bodies.

Note here that a parent strain of the *Aspergillus oryzae* strain AMA 1201-P is a strain AMA 1201; while a parent strain of the *Aspergillus oryzae* strain KBN 6217-56 is KBN 6217 strain. Both strains were obtained by separating resistant strain of 5-Fluoroorotic acid (5-FOA) in accordance with Mol. Gen. Genet. (1987) 210: 460-461, and thereafter selecting uridine requiring mutant strain.

*Aspergillus oryzae* strain AMA 1201 is deposited as follows.

Accession number FERM P-19089

International depositary: National Institute of Advanced Industrial Science and Technology, International Patent Organism Depositary, of which address is Chuo No. 6, 1-3, Higashi 1-chome, Tsukuba-shi, Ibaraki-ken, 305-8566, Japan.

Deposited date: Nov. 1, 2002

Similarly, *Aspergillus oryzae* strain KBN6217 is deposited as follows.

Accession number FERM P-19088

International depositary: National Institute of Advanced Industrial Science and Technology, International Patent Organism Depositary, of which address is Chuo No. 6, 1-3, Higashi 1-chome, Tsukuba-shi, Ibaraki-ken, 305-8566, Japan.

Deposited date: Nov. 1, 2002

Next, by using the protoplast obtained as mentioned above, by the method by Turner et al., (Gene, 36, 321-331(1985)), preparation of competent cells and transformation were carried out, and for each host, several tens of strains of trnasformants capable of growing in a medium without containing uridine (Czapek-Dox agar medium (0.2% NaNO$_3$, 0.1% K$_2$HPO$_4$, 0.05% KCl, 0.05% MgSO$_4$.7H$_2$O, 2% glucose (pH5.5)).

2. Obtaining Strain Producing Amylase with High Productivity

Transformants obtained in the above 1. were inoculated dottedly on an agar medium for detecting amylase activity (2% maltose, 1% amylopectin, 0.15% KH$_2$PO$_4$, 0.05% KCl, 0.09% NaNO$_3$, 0.05% MgSO$_4$.7H$_2$O, 1.5% Agar (pH6.5)). The size of halo generated by degradation of amylopectin of the substrate due to the effect of amylase secreted from fungus body was used as an index, strains producing amylase with high productivity were screened for each host.

3. Measurement of Amylase Activity

The strain producing amylase with high productivity obtained in the above 2. was scraped out by an applicator, and inoculated on 100 ml of SP medium (1% Starch, 1% polypeptone, 0. 5% KH$_2$PO$_4$, 0.1% NaNO$_3$, 0.05% MgSO$_4$.7H$_2$O (pH6.5)) and cultured with shaking at 30° C. for 66 hours. Thereafter, the amylase activity was measured in accordance with Example 6.

The measurement results are shown in Table of FIG. 11. In any cases where a strain producing amylase with low productivity AMA 1201-P or a strain producing amylase with high productivity KBN 6217-56 is used as a host, the production of amylase by a transformant is significantly increased as compared with that of the parent strain. Specifically, in a transformed strain obtained by using a strain producing amylase with low productivity AMA 1201-P as a host, the amount of production of amylase was 57 times or more as compared with that of the parent strain. On the other hand, in the transformed strain using a strain capable of originally producing amylase with high productivity, the productivity of amylase in the transformed strain was 10 times or more as compared with that of the parent strain. As mentioned above, it was confirmed that also in the case where *Aspergillus oryzae* was used as a host, the modified promoter of the present invention functioned effectively.

EXAMPLE 17

Construction of Plasmid for Expressing Heterologous Gene (Laccase Gene)

Next, the effect of a modified promoter in expressing a heterologous gene was investigated. A plasmid for expressing a laccase gene was constructed as follows. Firstly, in order to be linked to laccase gene, by a PCR reaction using the following primers, mutation was introduced into a Taka-amylase promoter and modified promoters (PCSPb and PCSPPb), respectively.

Primer at the 5'-end side of a Taka-amylase gene promoter (including an EcoRI cutting site):

5'-GGAATTCATGGTGTTTTGATC-3'   (Taa1F, SEQ ID NO: 35)

Primer for adding an EcoI22I cutting site to the 3'-end side of a Taka-amylase gene:

(Taa-E, SEQ ID NO: 36)
5'-GAGACCACCACGCGACATGCATAAATGCCTTCTGTGG-3'

On the other hand, in order to allow a laccase gene derived from genus *Paraphaeoshaeria* or a strain KL112 that is identified to be allied to this genus to link to a promoter and be integrated into a vector, mutation was introduced for amplification of laccase gene and recognition of restriction enzyme by a PCR reaction using the following primers.

Primer for amplifying laccase gene and for adding an EcoT22I cutting site to the 5'-end side: P11:

5'-CCATGCATTTCTTTATCATTGGAG-3'   (SEQ ID NO: 37)

Primer for amplifying laccase gene and for adding a SacI cutting site to the 3'-end side:, P12:

(SEQ ID NO: 38)
5'-CCGAGCTCTGGTATAGTATCTTGAATGTATC-3'

A template DNA to be used for a PCR reaction was prepared by using a strain KL112 cultured in a potato dextrose agar medium in accordance with the method by Raeder et al. (U. Raeder and P. Broda, Lett. Appl. Microb., 1, 17-20 (1985)). Note here that the strain KL112 is deposited as follows.

Accession number FERM P-19071

International depositary: National Institute of Advanced Industrial Science and Technology, International Patent Organism Depositary, of which address is Chuo No. 6, 1-3, Higashi 1-chome, Tsukuba-shi, Ibaraki-ken, 305-8566, Japan.

Deposited date: Oct. 18, 2002

Each promoter region mutated as mentioned above was cut with EcoRI and EcoT22I. On the other hand, amplified laccase gene was cut with EcoT22I and SacI. Then, restriction enzyme-cut fragments were collected and purified by agarose gel electrophoresis. The obtained restriction enzyme-cut fragments were inserted into EcoRI-SacI cutting site of an expression vector pYRG100 to construct a vector for expressing laccase pTALC100 (Taka-amylase promoter), pTALCPb (a modified promoter, PCSPb) and pTALCPPb (a modified promoter, PCSPPb).

EXAMPLE 18

Obtaining Transformant Using *Aspergillus Oryzae* as a Host

1. Obtaining Strains Producing Laccase with High Productivity

By using the plasmids pTALC100, pTALCPb and pTAL-CPPb prepared in Example 17, *Aspergillus oryzae* strain AMA 1201-P was transformed by the same method as described in Example 16-1. Then, the transformants were inoculated dottedly on an agar medium for detecting a laccase activity (a potato dextrose agar medium (DIFCO), 10 mM $CuSO_4$, 1 mM Cafeic acid), and halo generated by browning material generated by oxidation cleavage and polymerization of Cafeic acid of the substrate because of the effect of laccase secreted from fungus body was used as an index, strains producing amylase with high productivity were screened.

2. Measurement of Laccase Activity

The strain producing laccase with high productivity obtained in the above 1 was scraped out by an applicator, and inoculated in 50 ml of SPN medium (3% Starch, 1% polypeptone, 1% fermented residue, 0.1% $KH_2PO_4$, 0.2% KCl, 0.05% $MgSO_4.7H_2O$, 10 mM $CuSO_4$ (pH6.5)) and cultured with shaking at 30° C. for 6 days. After culturing, fungus bodies and supernatant were separated from each other by using a Buchner funnel and filter paper, and the supernatant was used as an enzyme solution.

Laccase activity was measured by examining the change in the absorbance at 430 nm when 2.5 ml of reaction system was prepared by adding an enzyme solution to 50 mM sodium acetate buffer and 1 mM guaiacol (Wako Pure Chemical Industries, Ltd.) and reacted at 40° C. for 10 minutes.

The measurement results are shown in Table of FIG. 12. In non-recombinant strain (*Aspergillus oryzae* strain AMA 1201-p used as a host), no laccase activity was observed. However, in any transformants, the high laccase activities were detected. The productivity of laccase of transformant in which a promoter (PCSPb) including three CCAAT-SRE fragments were introduced was the same level as that of the transformant in which a wild type promoter was introduced. However, by introducing the promoter (PCSPPb) including four CCAAT-SRE fragments, it was possible to obtain a strain capable of producing laccase with higher productivity.

From the above-mentioned results, even in the case where a heterogeneous gene was intended to be expressed, it was confirmed that the use of a modified promoter including a larger number of CCAAT-SRE sequences was advantageous in efficiently producing enzyme.

Note here that when the transformant culture filtrates were subjected to SDS-polyacrylamide gel electrophoresis, the amount of proteins expected from a laccase gene was apparently increased as compared with non-recombinant in any transformants.

INDUSTRIAL APPLICABILITY

According to the present invention, a modified promoter having high expression efficiency and functioning in filamentous fungi is provided. By using this modified promoter, an efficient production system of homogeneous and heterogeneous proteins using a filamentous fungus as a host can be constructed. When the amylase was investigated as a model of the production protein, transformant having not less than 7 times expression amount was obtained as compared with the case where a wild type promoter was used. Thus, it was confirmed that the modified promoter of the present invention was extremely useful in construction of a production system capable of producing proteins with high productivity.

The invention claimed is:

1. A modified Taka-amylase promoter from *Aspergillus oryzae* comprising two or more CCAAT-SRE enhancer sequences 5' upstream of a TATA box, wherein each of said two or more CCAAT-SRE enhancer sequences comprise a CCAAT sequence consisting of 5'-CCAATNNNNNN-3' (SEQ ID NO: 1) and an SRE sequence consisting of 5'-CG-GNNNNNNNNNGG-3' (SEQ ID NO: 2) wherein said CCAAT sequence is 5' upstream of said SRE sequence; wherein the modified promoter does not include a CCAAT sequence or SRE sequence between said TATA box and the CCAAT-SRE enhancer sequence proximal to said TATA box; and wherein the modified promoter is capable of functioning in a filamentous fungus.

2. The modified promoter according to claim 1, wherein CCAATNNNNNN is CCAATTAGAAG (SEQ ID NO:3).

3. The modified promoter according to claim 1, wherein CGGNNNNNNNNNGG is CGGHNWWWNWHGG (SEQ ID NO:4).

4. The modified promoter according to claim 1, wherein each of said two or more enhancer sequences consists of the nucleotide sequence of SEQ ID NO: 9.

5. A vector in which the modified promoter according to claim 1 is integrated.

6. A vector in which the modified promoter according to claim 1 is integrated and further a structural gene of a targeted protein is integrated under control of the modified promoter.

7. A transformed filamentous fungus comprising the vector according to claim 6 capable of expressing said structural gene.

8. A isolated filamentous fungus comprising the modified promoter according to claim 1, and a structure gene encoding a targeted protein and being under control of the modified promoter.

9. A method for producing a protein, the method comprising:
    culturing the filamentous fungus according to claim 8 under conditions capable of producing protein; and collecting the produced protein.

10. The modified promoter according to claim 1, comprising a CCAAT sequence consisting of SEQ ID NO: 3 and an SRE sequence consisting of SEQ ID NO: 4.

* * * * *